(12) United States Patent
Moseley et al.

(10) Patent No.: US 12,714,578 B2
(45) Date of Patent: Aug. 25, 2026

(54) BONY FUSION IMPLANT, INSERTION INSTRUMENT, AND METHODS

(71) Applicant: Spinal Simplicity, LLC, Overland Park, KS (US)

(72) Inventors: Todd Moseley, Olathe, KS (US); Luke Luallin, Fairway, KS (US); Adam Rogers, Olathe, KS (US); Christian Aragonez, Kansas City, MO (US); Jeff Slover, Lee's Summit, MO (US); Tony Hartlage, Prospect, KY (US)

(73) Assignee: Spinal Simplicity, LLC, Overland Park, KS (US)

( * ) Notice: Subject to any disclaimer, the term of this patent is extended or adjusted under 35 U.S.C. 154(b) by 53 days.

(21) Appl. No.: 18/924,287

(22) Filed: Oct. 23, 2024

(65) Prior Publication Data

US 2025/0143763 A1 May 8, 2025

Related U.S. Application Data

(63) Continuation-in-part of application No. 18/745,489, filed on Jun. 17, 2024, which is a continuation of (Continued)

(51) Int. Cl.
*A61F 2/46* (2006.01)
*A61B 17/70* (2006.01)
(Continued)

(52) U.S. Cl.
CPC ........ *A61F 2/4611* (2013.01); *A61B 17/7055* (2013.01); *A61B 17/864* (2013.01); (Continued)

(58) Field of Classification Search
CPC ..................................................... A61F 2/4611
See application file for complete search history.

(56) References Cited

U.S. PATENT DOCUMENTS 7,648,509 B2 1/2010 Stark
9,717,538 B2 8/2017 Chin et al.
(Continued)

FOREIGN PATENT DOCUMENTS

WO 2019152737 A1 8/2019
WO 2023052844 A2 4/2023
(Continued)

OTHER PUBLICATIONS

Allumin8, A Interger8 3D Porous Pedicle Screw, Orthopedics This Week, Dec. 18, 2023, https://allumin8.com.

(Continued)

*Primary Examiner* — Christian A Sevilla
(74) *Attorney, Agent, or Firm* — Erise IP, P.A.

(57) ABSTRACT

Systems, methods, and devices for bony fusion are disclosed. A threaded cannulated implant may be inserted into a target space, such as in the sacroiliac joint. The implant may have a distal section, a proximal section, and a central section between the distal section and the proximal section. The distal section may comprise cutting threads and flutes for self-drilling the implant into bone. The proximal section may be configured to couple to an insertion instrument for the implant. The central section may have a lattice structure through which bone graft may flow to promote bone ingrowth. A solid core region may be located inwards from the lattice structure. The central section may also have openings through the core region to connect the lattice structure to the cannula.

20 Claims, 14 Drawing Sheets

Related U.S. Application Data application No. 18/504,480, filed on Nov. 8, 2023, now Pat. No. 12,035,953.

(51) Int. Cl.

| | |
|---|---|
| ***A61B 17/86*** | (2006.01) |
| ***A61F 2/30*** | (2006.01) |
| ***A61F 2/44*** | (2006.01) |
| ***A61L 27/44*** | (2006.01) |

(52) U.S. Cl.

CPC ........ *A61F 2/30988* (2013.01); *A61F 2/4455* (2013.01); *A61L 27/44* (2013.01); *A61F 2002/30995* (2013.01)

(56) References Cited

U.S. PATENT DOCUMENTS

| | | | |
|---|---|---|---|
| 9,839,448 B2 | 12/2017 | Reckling et al. | |
| 9,931,212 B1 | 4/2018 | Donner et al. | |
| 10,058,430 B2 | 8/2018 | Donner et al. | |
| 10,179,014 B1 | 1/2019 | Menmuir et al. | |
| 10,271,859 B2 | 4/2019 | Assell et al. | |
| 10,292,720 B2 | 5/2019 | Donner | |
| 10,357,368 B2 | 7/2019 | Aksu | |
| 10,426,539 B2 | 10/2019 | Schifano et al. | |
| 10,595,917 B2 | 3/2020 | Loftus | |
| 10,631,905 B2 | 4/2020 | Asfora et al. | |
| 10,667,923 B2 | 6/2020 | Sullivan et al. | |
| 10,687,828 B2 | 6/2020 | Greenhalgh et al. | |
| 10,813,679 B2 | 10/2020 | Lanois et al. | |
| 10,940,008 B2 | 3/2021 | Patel | |
| 10,993,754 B2 | 5/2021 | Kuntz et al. | |
| 11,000,316 B2 | 5/2021 | Jimenez | |
| 11,045,231 B2 | 6/2021 | Stark | |
| 11,147,688 B2 | 10/2021 | Reckling et al. | |
| 11,172,939 B2 | 11/2021 | Donner et al. | |
| 11,172,969 B2 | 11/2021 | Suddaby | |
| 11,246,631 B2 | 2/2022 | Castro | |
| 11,389,305 B2 | 7/2022 | LaNeve et al. | |
| 11,446,070 B2 | 9/2022 | Kuntz et al. | |
| 11,471,203 B2 | 10/2022 | Sutika | |
| 11,504,166 B2 | 11/2022 | Kraus | |
| 11,628,004 B2 | 4/2023 | Lanois et al. | |
| 11,633,292 B2 | 4/2023 | Reiley | |
| 11,826,084 B2 | 11/2023 | Crossgrove et al. | |
| 11,857,420 B2 | 1/2024 | Mullin | |
| 12,035,953 B1 | 7/2024 | Moseley et al. | |
| 12,083,026 B2 | 9/2024 | Reckling et al. | |
| 2003/0065333 A1* | 4/2003 | DeMayo | A61B 17/7095 606/92 |
| 2007/0213655 A1* | 9/2007 | Prusmack | A61B 17/3472 604/57 |
| 2009/0216238 A1* | 8/2009 | Stark | A61F 2/4657 606/329 |
| 2014/0277460 A1* | 9/2014 | Schifano | A61B 17/8605 606/86 R |
| 2015/0012051 A1 | 1/2015 | Warren et al. | |
| 2016/0120661 A1 | 5/2016 | Schell et al. | |
| 2016/0250042 A1* | 9/2016 | Wahl | A61F 2/30756 623/18.11 |
| 2017/0258498 A1 | 9/2017 | Redmond et al. | |
| 2020/0085474 A1 | 3/2020 | Harshman et al. | |
| 2020/0268518 A1 | 8/2020 | Suh et al. | |
| 2020/0281729 A1 | 9/2020 | Schifano et al. | |
| 2021/0212833 A1 | 7/2021 | Chin et al. | |
| 2021/0244453 A1 | 8/2021 | Degeorge, Jr. et al. | |
| 2022/0192711 A1 | 6/2022 | Biedermann et al. | |
| 2022/0304672 A1 | 9/2022 | Kalhorn et al. | |
| 2022/0354654 A1 | 11/2022 | Lewis et al. | |
| 2023/0181322 A1 | 6/2023 | Greenhalgh et al. | |
| 2023/0329871 A1 | 10/2023 | Greenhalgh et al. | |
| 2023/0390078 A1 | 12/2023 | Bergey | |
| 2024/0091026 A1 | 3/2024 | Arnold et al. | |
| 2024/0115296 A1 | 4/2024 | Huffmann et al. | |

FOREIGN PATENT DOCUMENTS

| | | |
|---|---|---|
| WO | 2023056347 A1 | 4/2023 |
| WO | 2023137124 A2 | 7/2023 |
| WO | 2024098047 A1 | 5/2024 |
| WO | 2024098048 A1 | 5/2024 |
| WO | 2024098049 A2 | 5/2024 |
| WO | 2024119118 A1 | 6/2024 |

OTHER PUBLICATIONS

PCT Patent Application PCT/US2023/082670 International Search Report and The Written Opinion, issued Aug. 8, 2024.

PCT Patent Application PCT/US2023/082673 International Search Report and The Written Opinion, issued Mar. 21, 2024.

U.S. Appl. No. 63/249,945, filed Sep. 29, 2021.

U.S. Appl. No. 18/504,635 Non-Final Office Action issued Jun. 27, 2024.

U.S. Appl. No. 18/504,635 Non-Final Office Action issued May 1, 2024.

European Patent Application 25209000.6, Partial Supplementary Search Report, issued Mar. 3, 2026.

European Patent Application 25209000.6, Extended European Search Report, issued May 7, 2026.

* cited by examiner 196
164b
188
190b
164a
166
190a

BONY FUSION IMPLANT, INSERTION INSTRUMENT, AND METHODS

CROSS-REFERENCE TO RELATED APPLICATIONS

This non-provisional patent application is a continuation-in-part and claims prior benefit, with regard to all common subject matter, of earlier-filed U.S. patent application Ser. No. 18/745,489, filed Jun. 17, 2024, and entitled "BONY FUSION IMPLANT, INSERTION INSTRUMENT, AND METHODS", which is a continuation of U.S. patent application Ser. No. 18/504,480, filed Nov. 8, 2023, now U.S. Pat. No. 12,035,953, and entitled "BONY FUSION IMPLANT, INSERTION INSTRUMENT, AND METHODS".

This non-provisional patent application shares certain common subject matter with U.S. application Ser. No. 18/504,635, filed Nov. 8, 2023, and entitled "SYSTEMS, METHODS, AND DEVICES FOR LATERAL AND POSTERIOR SACROILIAC JOINT FUSION." The above-identified applications and patents are hereby incorporated by reference in its entirety.

TECHNICAL FIELD

Embodiments of the present disclosure generally relate to systems, devices, and methods for bony fusion. More specifically, embodiments of the present disclosure relate to implants having an open architecture for fusion and stabilization of bones and insertion instruments and methods therefor.

RELATED ART

The spine consists of a column of twenty-four vertebrae that extends from the skull to the hips. The most inferior lumbar vertebra (L5) connects to the sacrum, which is a large bone that is formed by the fusion of the sacral vertebrae. On each side of the sacrum is an ilium, and the sacrum articulates with each ilium to form two sacroiliac (SI) joints. The SI joints play a significant role in absorbing impact from walking, lifting, and other movements.

When the ligaments or bony surfaces are damaged (e.g., due to trauma, arthritis, or other conditions), the SI joints can be a source of intense pain that can radiate into the leg. Inflammation in the SI joints is known as sacroiliitis. Sacroiliitis can be treated via non-surgical and surgical methods. Sacroiliitis may be treated surgically via an SI joint fusion procedure that uses an implant device to provide stability. Typical posterior SI joint implants are not made out of metal, leading to lower strength, and are deficient in promoting bone ingrowth. Additionally, posterior SI implants commonly are wedge shaped and are impacted into the SI joint and have a risk of working their way back out of the SI joint. Implants with improved control of insertion and that mitigate back out are needed. Other regions of the body may require the use of a bone screw for stabilization of bone, such as the foot, ankle, craniomaxillofacial, or the like. Improvements in bony fusion devices are needed.

SUMMARY

In some embodiments, the techniques described herein relate to an implant for bony fusion at a target space, including: a plurality of external threads extending along a length of the implant; a cannula extending along a longitudinal axis of the implant; a distal section; a proximal section configured to be coupled to an insertion instrument; and a central section between the proximal section and the distal section, the central section including: an interior core region adjacent to the cannula; a lattice structure located laterally between the interior core region and a minor diameter of the plurality of external threads; and a plurality of openings extending through the interior core region, the plurality of openings connecting the lattice structure to the cannula.

In some embodiments, the techniques described herein relate to an implant, wherein the implant is configured to be packed with bone graft, and wherein the plurality of openings is connected to the lattice structure such that the bone graft flows between the plurality of openings and the lattice structure.

In some embodiments, the techniques described herein relate to an implant, wherein the distal section includes at least one cutting flute for self-drilling the implant into the target space.

In some embodiments, the techniques described herein relate to an implant, wherein the proximal section includes internal threading for threadedly engaging the insertion instrument, wherein rotation of the insertion instrument rotates the implant for insertion into the target space.

In some embodiments, the techniques described herein relate to an implant, wherein at least a portion of the plurality of external threads includes at least one thread heel configured to reduce proximal movement of the implant when inserted into the target space.

In some embodiments, the techniques described herein relate to an implant, wherein the at least one thread heel is oriented in a first direction to prevent interference with threading of the implant during insertion.

In some embodiments, the techniques described herein relate to an implant, wherein the central section includes a length of about 30% to about 60% of the length of the implant.

In some embodiments, the techniques described herein relate to an implant, wherein the implant is formed from at least one of: a titanium alloy, stainless steel, magnesium, a polymer, a bioresorbable material, or an allograft, and wherein the implant is coated with hydroxyapatite.

In some embodiments, the techniques described herein relate to an implant for bony fusion of a target space, including: a cannula along a longitudinal axis of the implant; a distal section configured to self-drill the implant into bone; a proximal section; and a central section between the distal section and the proximal section, including: a lattice structure fluidly connected to the cannula, wherein the lattice structure is configured to receive bone graft for bone ingrowth of the implant, wherein the implant includes a plurality of external threads extending along a length of the implant.

In some embodiments, the techniques described herein relate to an implant, wherein the central section further includes: a core region adjacent to the cannula, and a plurality of fenestrations extending through the core region to fluidly connect the cannula to the lattice structure.

In some embodiments, the techniques described herein relate to an implant, wherein the lattice structure extends laterally from a perimeter of the core region to a minor diameter of the plurality of external threads.

In some embodiments, the techniques described herein relate to an implant, wherein the plurality of fenestrations follows a thread path of the plurality of external threads.

In some embodiments, the techniques described herein relate to an implant, wherein the implant includes a variable diameter that increases from the distal section to the proximal section.

In some embodiments, the techniques described herein relate to an implant, wherein the target space is a sacroiliac joint, and wherein the plurality of external threads of the implant is configured to embed into a sacrum and an ilium of the sacroiliac joint.

In some embodiments, the techniques described herein relate to an implant, wherein the implant is configured to be inserted into the sacroiliac joint via a posterior approach.

In some embodiments, the techniques described herein relate to an implant, wherein the proximal section includes a plurality of internal threads and a plurality of recesses configured for coupling to an insertion instrument.

In some embodiments, the techniques described herein relate to a method for bony fusion of a target space, including: providing an implant having a cannula along a longitudinal axis, including: a plurality of external threads extending along a length of the implant; a distal section; a proximal section configured to be coupled to an insertion instrument; and a central section between the proximal section and the distal section, the central section including: an interior core region adjacent to the cannula; a lattice structure located laterally between the interior core region and a minor diameter of the plurality of external threads; and a plurality of openings extending through the interior core region, the plurality of openings connecting the lattice structure to the cannula; and providing instructions, the instructions including steps of: couple the implant to the insertion instrument; and insert the implant into the target space using the insertion instrument.

In some embodiments, the techniques described herein relate to a method, wherein the instructions further include: make a minimally invasive incision; successively insert a series of dilators into the minimally invasive incision to create a working channel; and dock into the target space using a final dilator, the final dilator including at least one distal tang to engage with the target space.

In some embodiments, the techniques described herein relate to a method, wherein the distal section includes cutting threads and flutes configured to self-drill the implant into the target space.

In some embodiments, the techniques described herein relate to a method, wherein the instructions further include: pack the implant with bone graft, wherein the bone graft flows from between the cannula, the plurality of openings, and the lattice structure.

In some embodiments, the techniques described herein relate to an insertion system for inserting a posterior sacroiliac (SI) joint implant, including: a guidewire; an insertion instrument, including: a cannulated rod configured to be inserted over the guidewire, the cannulated rod including: a rod distal end including a first set of external threads for threadedly engaging with the posterior SI joint implant; and a rod proximal end including a female luer lock, wherein the female luer lock is configured to couple the insertion instrument to a syringe such that bone graft is insertable into the posterior SI joint implant by the syringe and through the cannulated rod; and a rotational feature coupled to the rod proximal end and configured to be rotated by an operator to rotate the cannulated rod to threadedly engage the cannulated rod with the posterior SI joint implant.

In some embodiments, the techniques described herein relate to an insertion system, wherein the insertion instrument further includes: an outer shaft that receives the cannulated rod, the outer shaft including: a shaft distal end including at least one coupling member for coupling to the posterior SI joint implant; and a shaft proximal end.

In some embodiments, the techniques described herein relate to an insertion system, wherein the shaft proximal end includes internal threads, and wherein the rod proximal end includes a second set of external threads configured to threadedly engage with the internal threads to couple the cannulated rod to the outer shaft.

In some embodiments, the techniques described herein relate to an insertion system, further including: a joint sleeve configured to be inserted into an SI joint and to receive the insertion instrument therein, the joint sleeve including: a first shoulder configured to engage with an ilium; and a second shoulder configured to engage with a sacrum.

In some embodiments, the techniques described herein relate to an insertion system, wherein the first shoulder has a first height distinct from a second height of the second shoulder.

In some embodiments, the techniques described herein relate to an insertion system, wherein the rotational feature is a knob having an opening therethrough to provide access to the female luer lock.

In some embodiments, the techniques described herein relate to an insertion system for inserting an implant, including: a guidewire; an insertion instrument, including: a cannulated rod configured to be inserted over the guidewire and to be coupled to the implant, including: a rod distal end for coupling to the implant; and a rod proximal end having a syringe connector, wherein the syringe connector is configured to couple to a syringe, thereby fluidly coupling the syringe, the insertion instrument, and the implant such that bone graft is deployable into the implant by the syringe and through the cannulated rod when the cannulated rod and the implant are coupled.

In some embodiments, the techniques described herein relate to an insertion system, wherein the rod distal end includes at least one first coupling feature for coupling the cannulated rod to the implant.

In some embodiments, the techniques described herein relate to an insertion system, further including: a shaft that receives the cannulated rod, the shaft including: a shaft distal end including at least one second coupling feature for coupling the shaft to the implant.

In some embodiments, the techniques described herein relate to an insertion system, wherein the at least one first coupling feature includes threads, and wherein the at least one second coupling feature includes at least one prong.

In some embodiments, the techniques described herein relate to an insertion system, wherein the rod proximal end includes external threads that mate with internal threads on a shaft proximal end of the shaft.

In some embodiments, the techniques described herein relate to an insertion system, wherein the implant is a posterior sacroiliac (SI) joint implant and further including: a joint sleeve configured to be inserted into an SI joint space and to receive the cannulated rod during insertion of the posterior SI joint implant, the joint sleeve including: a first shoulder configured to abut against an ilium; and a second shoulder opposite the first shoulder and that is configured to abut against a sacrum.

In some embodiments, the techniques described herein relate to an insertion system, wherein the first shoulder includes a first height distinct from a second height of the second shoulder.

In some embodiments, the techniques described herein relate to an insertion system, wherein the guidewire includes nitinol.

In some embodiments, the techniques described herein relate to a method for posterior sacroiliac (SI) joint fusion, including: providing an insertion instrument including: a cannulated rod having a rod distal end and a rod proximal end including a luer lock; creating a minimally invasive incision on a patient to provide posterior access to an SI joint of the patient; inserting a guidewire through the minimally invasive incision and into the SI joint of the patient; coupling the insertion instrument to a posterior SI joint implant; inserting, using the insertion instrument and through the minimally invasive incision, the posterior SI joint implant into the SI joint; coupling a syringe to the rod proximal end via the luer lock such that the syringe is fluidly connected to the insertion instrument and the posterior SI joint implant; and filling, using the syringe and through the insertion instrument, the posterior SI joint implant with bone graft.

In some embodiments, the techniques described herein relate to a method, further including: prior to inserting the posterior SI joint implant into the SI joint, inserting a joint sleeve through the minimally invasive incision, over the guidewire, and into the SI joint.

In some embodiments, the techniques described herein relate to a method, wherein the joint sleeve includes a first shoulder configured to engage with an ilium and a second shoulder configured to engage with a sacrum.

In some embodiments, the techniques described herein relate to a method, wherein coupling the insertion instrument to the posterior SI joint implant includes threadedly engaging a distal end of the cannulated rod with a proximal end of the posterior SI joint implant.

In some embodiments, the techniques described herein relate to a method, wherein the insertion instrument and the posterior SI joint implant are inserted over the guidewire.

In some embodiments, the techniques described herein relate to a method, further including: pre-filling the posterior SI joint implant with the bone graft before inserting the posterior SI joint implant into the SI joint.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current present disclosure will be apparent from the following detailed description of the embodiments and the accompanying drawing figures.

BRIEF DESCRIPTION OF THE FIGURES

Embodiments of the present disclosure are described in detail below with reference to the attached drawing figures, wherein.

Figure 1:
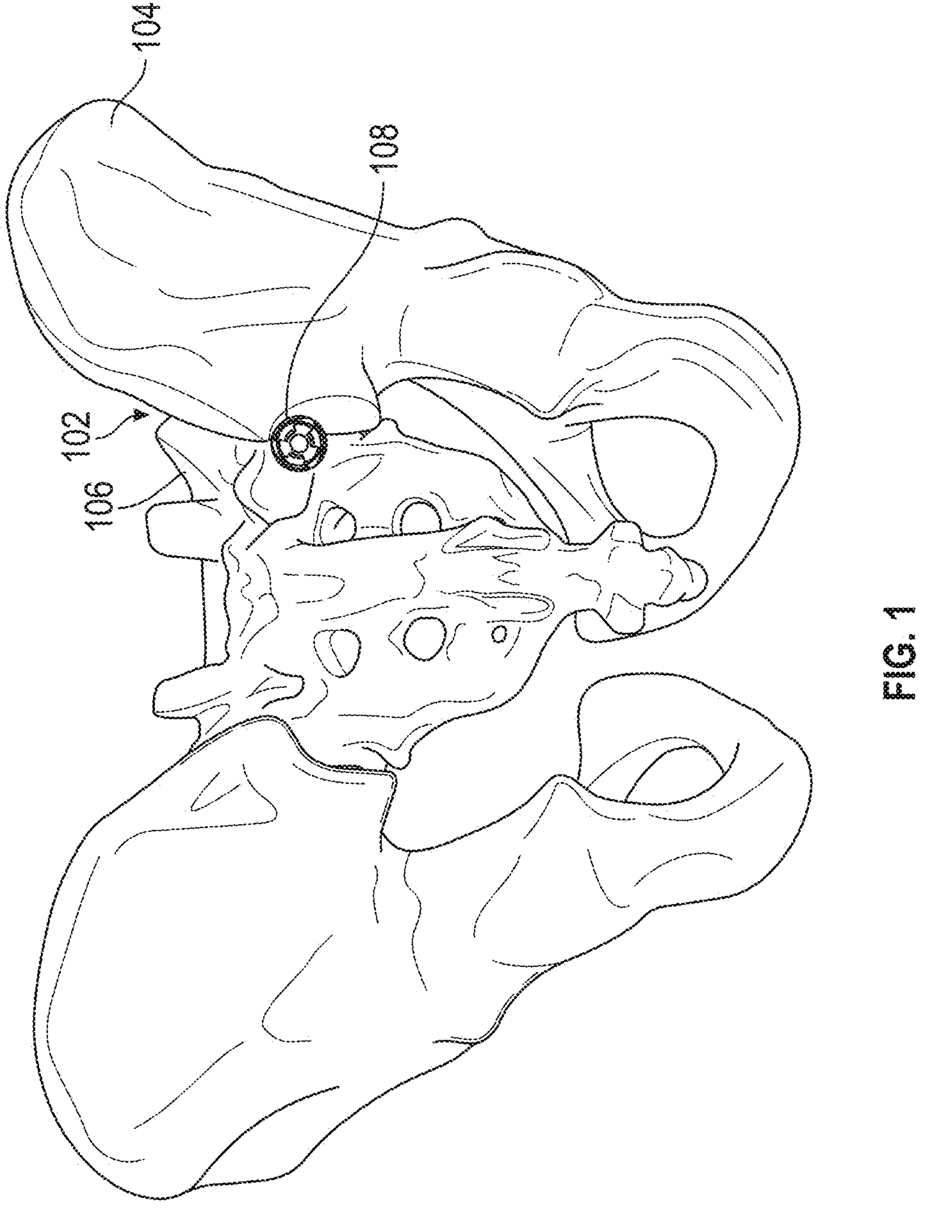
FIG. 1 illustrates an implant inserted in the sacroiliac joint for some embodiments.

The drawing figures do not limit the present disclosure to the specific embodiments disclosed and described herein. The drawings are not necessarily to scale, emphasis instead being placed upon clearly illustrating the principles of the present disclosure.

DETAILED DESCRIPTION

The subject matter of the present disclosure is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be understood by one skilled in the art and are intended to be captured within the scope of the claims. Terms should not be interpreted as implying any particular ordering of various steps described unless the order of individual steps is explicitly described.

The following detailed description of embodiments of the present disclosure references the accompanying drawings that illustrate specific embodiments in which the present disclosure can be practiced. The embodiments are intended to describe aspects of the present disclosure in sufficient detail to enable those skilled in the art to practice the present disclosure. Other embodiments can be utilized and changes can be made without departing from the scope of the present disclosure. The following detailed description is, therefore, not to be taken in a limiting sense. The scope of embodiments of the present disclosure is defined only by the appended claims, along with the full scope of equivalents to which such claims are entitled.

In this description, references to “one embodiment,” “an embodiment,” or “embodiments” mean that the feature or features being referred to are included in at least one embodiment of the technology. Separate reference to “one embodiment” “an embodiment”, or “embodiments” in this description do not necessarily refer to the same embodiment and are also not mutually exclusive unless so stated and/or except as will be readily apparent to those skilled in the art from the description. For example, a feature, structure, or act described in one embodiment may also be included in other embodiments but is not necessarily included. Thus, the technology can include a variety of combinations and/or integrations of the embodiments described herein.

Overview

Embodiments of the present disclosure are generally directed to systems, devices, and methods for stabilization and fusion of bones and/or joints, such as the sacroiliac (SI) joint 102, as shown in FIG. 1 depicting a perspective, posterior view of SI joint 102. The SI joint 102 is located between the ilium 104 and the sacrum 106 in the pelvic region of the body. An implant 108 may be inserted posteriorly into the SI joint 102 and wedged between the ilium 104 and the sacrum 106. The implant 108 may be placed in or proximal to the S1 vertebra of the sacrum 106. The implant 108 may be externally threaded, and the threads may help anchor implant 108 to ilium 104 and sacrum 106 on either side of SI joint 102.

The implant 108 may be inserted via a minimally invasive incision. A minimally invasive incision may comprise an incision of less than about 2 inches, in contrast to traditional open surgeries having five-to-six-inch incisions. Minimally invasive surgeries allow for muscle to be distracted as opposed to cut away as in open surgeries, which allows for quicker recoveries, reduced blood loss, and hospital stay, among other benefits.

The implant 108 may have a distal end configured to self-drill the implant 108 into bone, which may obviate the need to drill a pilot hole. A central section may extend proximally from the distal section and may have a lattice structure therein. A proximal section (shown in FIG. 1) may extend proximally from the central section and may be configured to receive an insertion tool for inserting implant 108 into the patient. The lattice structure may delineate the central section from the proximal and distal sections. The implant 108 may be cannulated along a length thereof. The open architecture provided by the cannula and the lattice structure may promote bone ingrowth (osseointegration) when implant 108 is implanted. Improving bone ingrowth may improve bony fusion, thereby increasing the stabilization of the bone. In contrast, typical posterior SI joint implants are solid structures that cannot be packed internally with bone graft and, as such, the bone ingrowth of such implants may be less than implant 108 described herein. The implant 108 may be formed from a metal or metal alloy, such as stainless steel or a titanium alloy. In some embodiments, the implant 108 may be formed from magnesium, a polymer, a bioresorbable material, or an allograft. In some embodiments, the implant 108 is formed by an additive manufacturing process, molding, machining, or any combination thereof. The implant 108 may also be coated with hydroxyapatite to promote bony fixation.

Implant

FIGS. 2A-2E illustrate various views of implant 108 for some embodiments of the present disclosure. Looking first at FIGS. 2A and 2B, a planar view and a cross-sectional view taken along the line A-A, respectively, are illustrated for some embodiments of the present disclosure.

As shown, implant 108 may comprise a distal section 110*a*, a proximal section 110*b*, and a central section 110*c* extending between distal section 110*a* and proximal section 110*b*. Implant 108 may comprise external threads 112 along a length thereof. In some embodiments, threads 112 extend entirely along implant 108. It is contemplated that a portion of implant 108 may be unthreaded. For example, proximal section 110*b* may be unthreaded. As described above, when inserted in SI joint 102, threads 112 may engage with ilium 104 and sacrum 106 to maintain the position of implant 108 within SI joint 102. The threaded engagement may reduce movement of implant 108 when inserted into SI joint 102.

In some embodiments, the major diameter of threads 112 increases from distal section 110*a* to proximal section 110*b*. Providing a larger diameter at proximal section 110*b* may provide implant 108 with a tighter fit when inserted into the final position, which may reduce the likelihood that the implant 108 moves once inserted. In some embodiments, the major diameter of threads 112 at distal section 110*a* is about 7 mm, and the major diameter of threads 112 at proximal section 110*b* is about 10 mm. In some embodiments, the threads 112 on distal section 110*a* may taper down towards the distal end of distal section 110*a*.

Threads 112 may be single lead threads, dual lead threads, tri-lead threads, quad lead threads, or any other thread type. Threads 112 may have a major diameter of about 7 mm to about 10 mm and a minor diameter of about 5 mm to about 8 mm in some embodiments. Generally, any thread dimensions may be employed, and it will be appreciated that the thread dimensions and other dimensions of implant 108 may vary based on where in the body implant 108 is configured to be inserted. For example, an implant 108 configured for insertion into SI joint 102 may have different thread dimensions than an implant 108 configured for insertion into the foot.

Figure 2B:
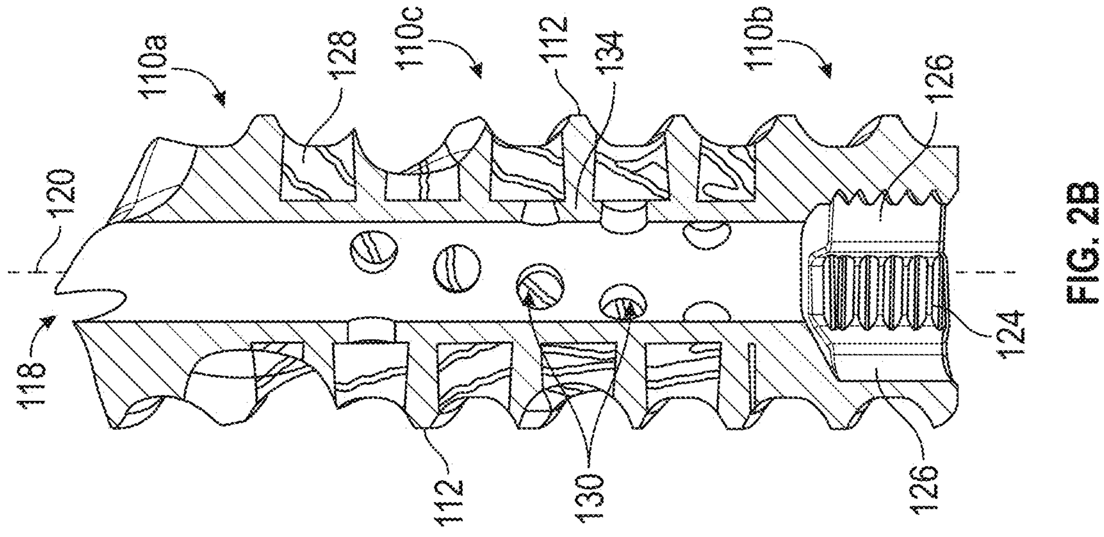
FIG. 2B illustrates a first cross-sectional view of the implant for some embodiments.
Figure 2A:
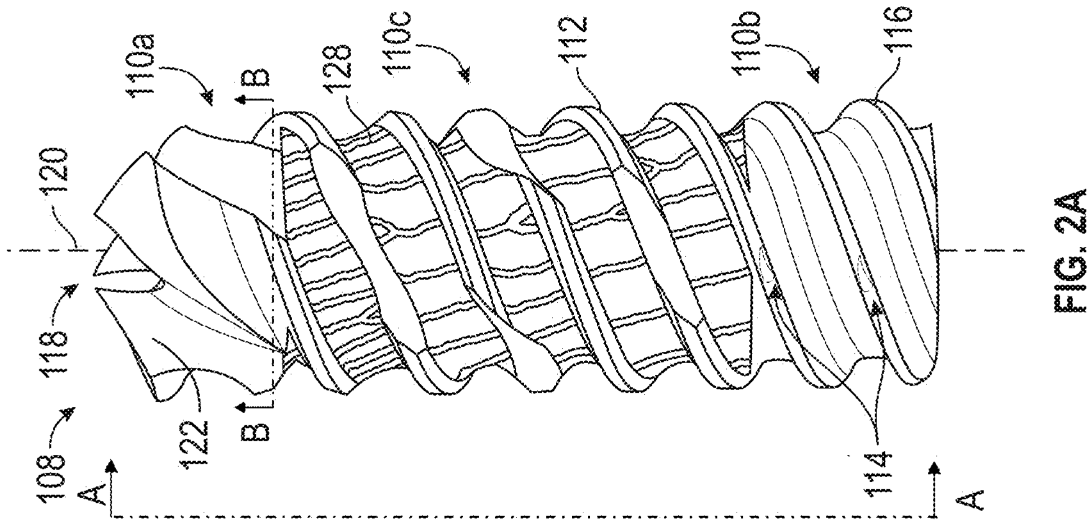
FIG. 2A illustrates a planar view of the implant for some embodiments.
Figures 2C, 2D:
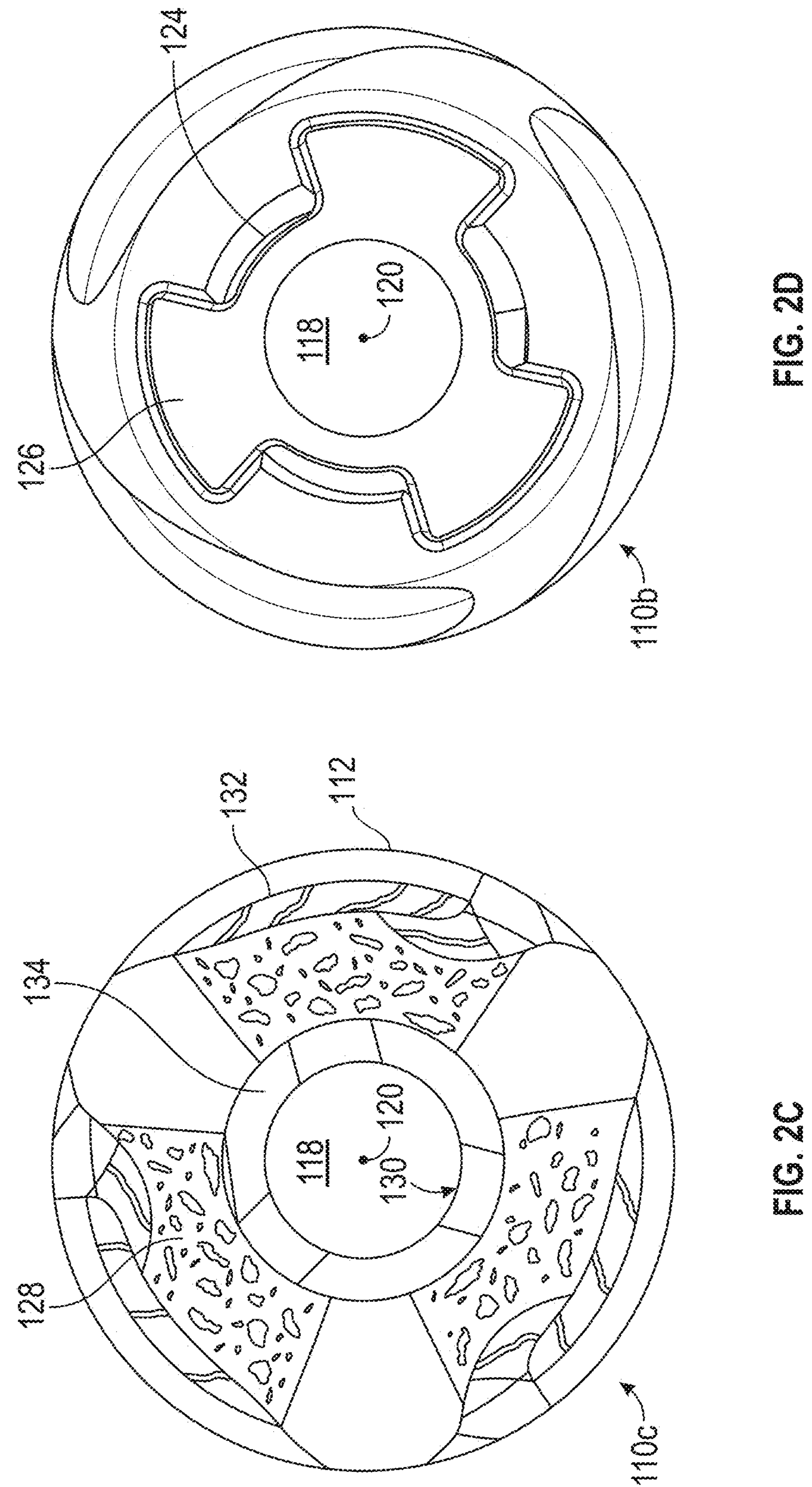
FIG. 2C illustrates a second cross-sectional view of the implant for some embodiments.
FIG. 2D illustrates a distal-looking view of the implant for some embodiments.
Figure 2E:
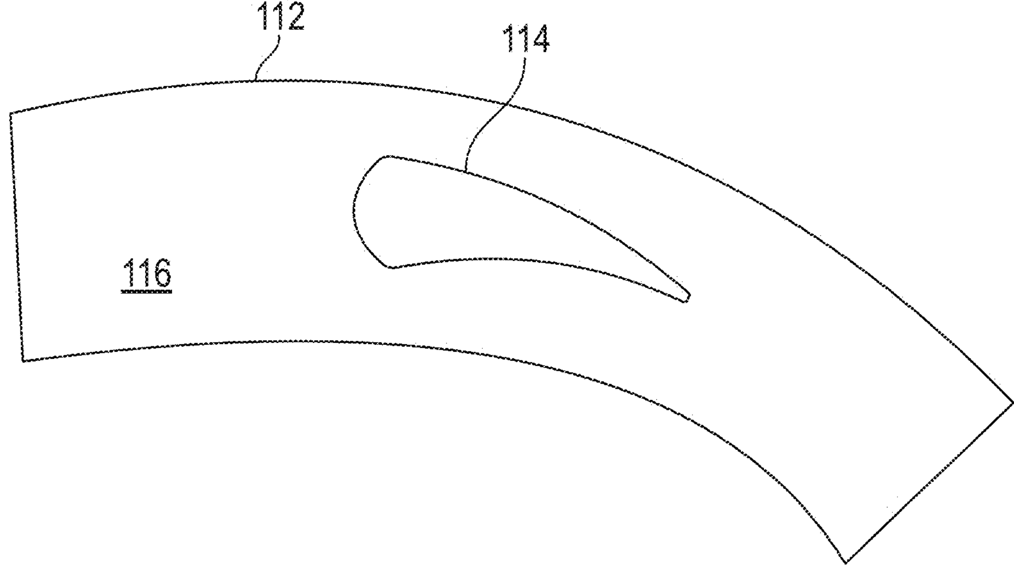
FIG. 2E illustrates a top-down view of a thread heel on a thread of the implant for some embodiments.

In some embodiments, and as shown in FIGS. 2A and 2E, threads 112 comprise heels 114 on an outer surface 116 of threads 112. The heels 114 (also referred to as hooks or teeth) may be a gripping feature configured to maintain the position/minimize movement of implant 108 in SI joint 102. When implant 108 is inserted into SI joint 102, heels 114 may at least partially embed into ilium 104 and sacrum 106 and resist movement of implant 108. Accordingly, back out of implant 108 from SI joint 102 may be mitigated.

As shown, heels 114 may be oriented in one direction. That is, heels may have a first end with a smaller width than a second end. For example, heels 114 may have a first end formed as a pointed tip and a second end formed as a blunt tip. The first end may be distal from the second end. Providing heels 114 with such a geometry may allow for heels 114 to not interfere (e.g., not resist) the threading of implant 108 into SI joint 102 while resisting any proximal motion of implant 108 out of SI joint 102. In some embodiments, heels 114 protrude from outer surface 116. In some embodiments, heels 114 protrude a height of about 1 mm above outer surface 116. In some embodiments, the height of heels 114 decreases from the second, wider end to the first, thinner end, or vice versa. In some embodiments, heels 114 are evenly spaced on threads 112 along the length of implant 108. In some embodiments, heels 114 are spaced along threads 112 by 15 degrees, 30 degrees, 45 degrees, 90 degrees, 180 degrees, or in any other increment. In some embodiments, the spacing between heels 114 is not even. For example, it may be advantageous to have more heels 114 and/or reduced spacing between heels 114 near proximal section 110*b* than near distal section 110*a* to aid in mitigating back out of implant 108. Generally, any number, arrangement, sizing, spacing, or any combination thereof of heels 114 on threads 112 is within the scope of the present disclosure.

In some embodiments, implant 108 has a cannula 118 extending along a length thereof. The cannula 118 may extend entirely through implant 108. In some embodiments, implant 108 may be symmetrical about a longitudinal axis 120, and cannula 118 may extend along longitudinal axis 120 such that cannula 118 presents a central bore through implant 108. In some embodiments, cannula 118 is sized to receive a guidewire therethrough such that implant 108 may be inserted over the guidewire. As shown in FIG. 2B, cannula 118 may have a variable diameter. For example, proximal section 110*b* may have a larger diameter to accommodate an insertion instrument (discussed below). In some embodiments, cannula 118 does not extend entirely through implant 108 such that distal section 110*a* is closed. In some embodiments, implant 108 does not comprise a cannula 118, presenting a solid structure. In some such embodiments, proximal section 110*b* may be formed with a recess as shown for coupling to an insertion instrument.

As discussed previously, distal section 110*a* may be configured for self-drilling implant 108 into bone such that a pilot hole may not need to be drilled into the patient. In some embodiments, distal section 110*a* comprises one or more flutes 122 that aid in self-drilling. Additionally, threads 112 may be sharp to aid in self-drilling. For example, threads 112 may be cutting threads or box threads configured to cut through bone. Threads 112 and/or flutes 122 may also self-harvest the drilled bone, which may further promote bone ingrowth of implant 108.

Looking now at FIGS. 2B and 2D, it can be seen that proximal section 110*b* may be configured for coupling to the insertion instrument. In some embodiments, proximal section 110*b* may comprise internal threads 124 and recesses 126. In some embodiments, each recess 126 mates with a corresponding prong of the insertion instrument, and internal threads 124 couple to a threaded rod of the insertion instrument. Accordingly, once coupled, the insertion instrument may be used to insert implant 108 into SI joint 102. When implant 108 is formed without a cannula 118, proximal section 110*b* may still comprise internal threads 124 and recesses 126, while distal section 110*a* and central section 110*c* may be solid through their center.

As shown in FIGS. 2A-2C, central section 110*c* may comprise a lattice structure 128 and openings 130 (also referred to as fenestrations). The portion of implant 108 that is distal from lattice structure 128 may be distal section 110*a*, and the portion of implant 108 that is proximal from 122 may be proximal section 110*b*. Providing a lattice structure 128 may reduce the overall weight of implant 108. Furthermore, the lattice structure 128 provides for open volume in which bone graft may flow to promote bone ingrowth. In some embodiments, implant 108 may be pre-packed and/or post-packed with bone graft to promote bony fusion. Openings 130 may fluidly connect cannula 118 to lattice structure 128, thereby allowing for bone graft to be packed via cannula 118 and travel into lattice structure 128. Openings 130 may follow the thread path of threads 112. By following the thread path of threads 112, bone ingrowth may be enabled across or through implant 108 from ilium 104 to sacrum 106. In some embodiments, openings 130 are arranged linearly in central section 110*c*. Generally, any arrangement of openings 130 within central section 110*c* is within the scope hereof. In some embodiments, central section 110*c* comprises a length of about 20% to about 80% of an overall length of implant 108. In some embodiments, central section 110*c* comprises a length of about 30% to about 60% of an overall length of implant 108. In some embodiments, central section 110*c* comprises a length of about 50% of an overall length of implant 108. In some embodiments, implant 108 comprises a length measured from proximal section 110*b* to distal section 110*a* of about 25 mm to about 35 mm.

Referring now to FIG. 2C, a cross-sectional, proximal-looking view taken along the lines B-B shown in FIG. 2A is illustrated for some embodiments. As shown, lattice structure 128 extends laterally substantially from a minor diameter 132 of threads 112 to a core region 134 of implant 108. The core region 134 may be an interior region of implant 108 through which lattice structure 128 does not extend. Core region 134 may be adjacent to cannula 118. Core region 134 may be generally solid; however, and as shown, openings 130 may extend through portions of core region 134 to fluidly connect cannula 118 to lattice structure 128. Accordingly, bone graft may be inserted into cannula 118 and flow into lattice structure 128 via openings 130. Furthermore, as seen best in FIG. 2B, the core region 134 is mechanically connected to the solid thread profile at various locations along the length of central section 110*c*, which improves the mechanical strength of implant 108 as compared to an implant in which lattice structure 128 was adjacent to cannula 118 (i.e., if core region 134 was not present).

As previously discussed, implant 108 may be additively manufactured. Accordingly, lattice structure 128 may be a software-generated lattice structure printed by an additive manufacturing device. In some embodiments, lattice structure 128 is a triply periodic minimal surface (TPMS) lattice. In some embodiments, lattice structure 128 is a split-P TPMS lattice, or may be any other TPMS lattice type. In some embodiments, lattice structure 128 is one of a cubic lattice, a pentagonal lattice, a hexagonal lattice, an octagonal lattice, or the like. Generally, any type of lattice structure may be used. The lattice structure 128 may be roughened, which may further promote bone ingrowth of implant 108. Further, lattice structure 128 may comprise more than one lattice type. For example, a first portion of lattice structure 128 may have a first lattice type and a second portion of lattice structure 128 may have a second lattice type. It is contemplated that the lattice structure may be selected and/or customized based on the specific anatomy of the patient.

In some embodiments, implant 108 is formed from a metal or metal alloy. In some embodiments, implant 108 is formed from a titanium or titanium alloy. In some embodiments, implant 108 comprises Ti-6Al-4V, which is an alpha-beta titanium alloy that provides a high specific strength and good corrosion resistance. It is contemplated that other alpha-beta titanium alloys may be used without departing from the scope hereof. For example, implant 108 may comprise Tl-6Al-7Nb. Other metal and metal alloys may be used such as, but not limited to, cobalt chrome, stainless steel, nitinol, or tantalum. In some embodiments, implant 108 is formed from a polymer, such as PEEK. In some embodiments, implant 108 is formed from a bioresorbable material such as a ceramic, hydroxyapatite, or magnesium.

Figure 3A:
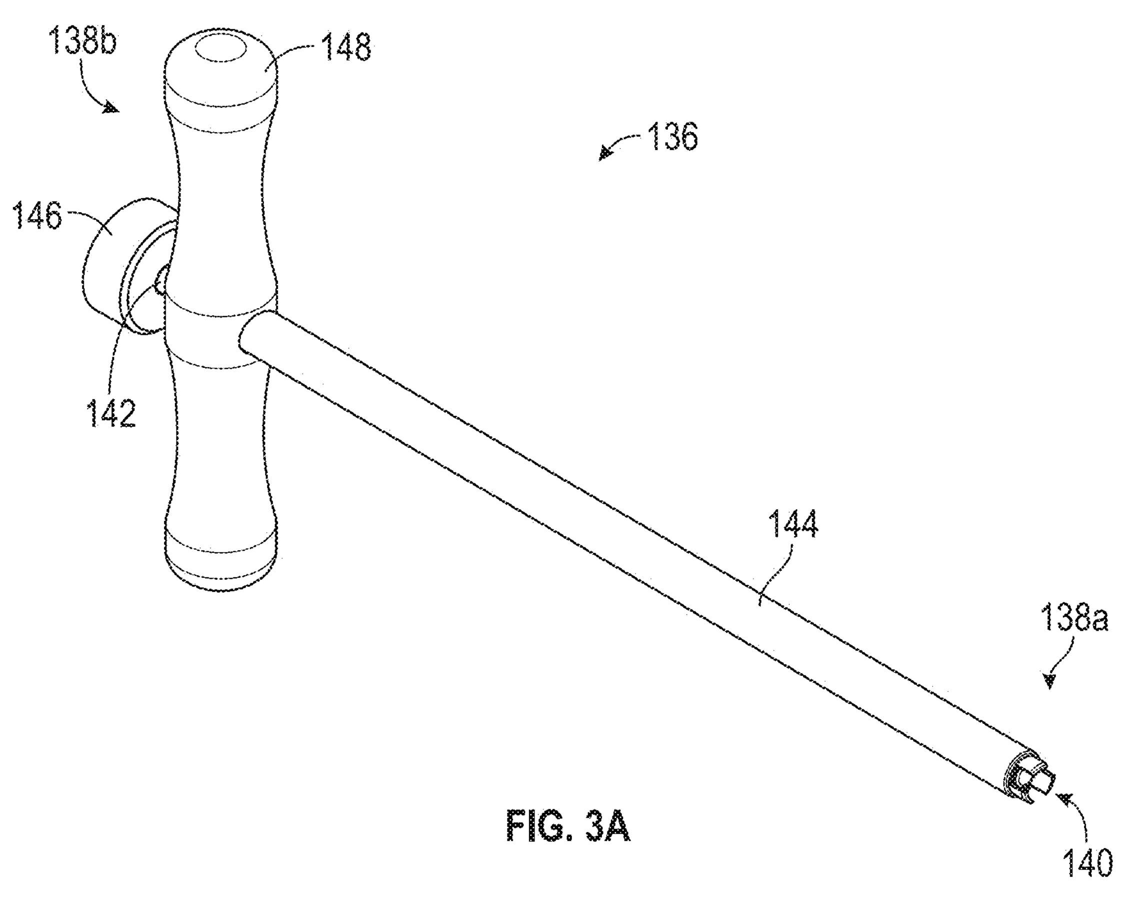
FIG. 3A illustrates a perspective view of an insertion instrument for some embodiments.
Figure 3B:
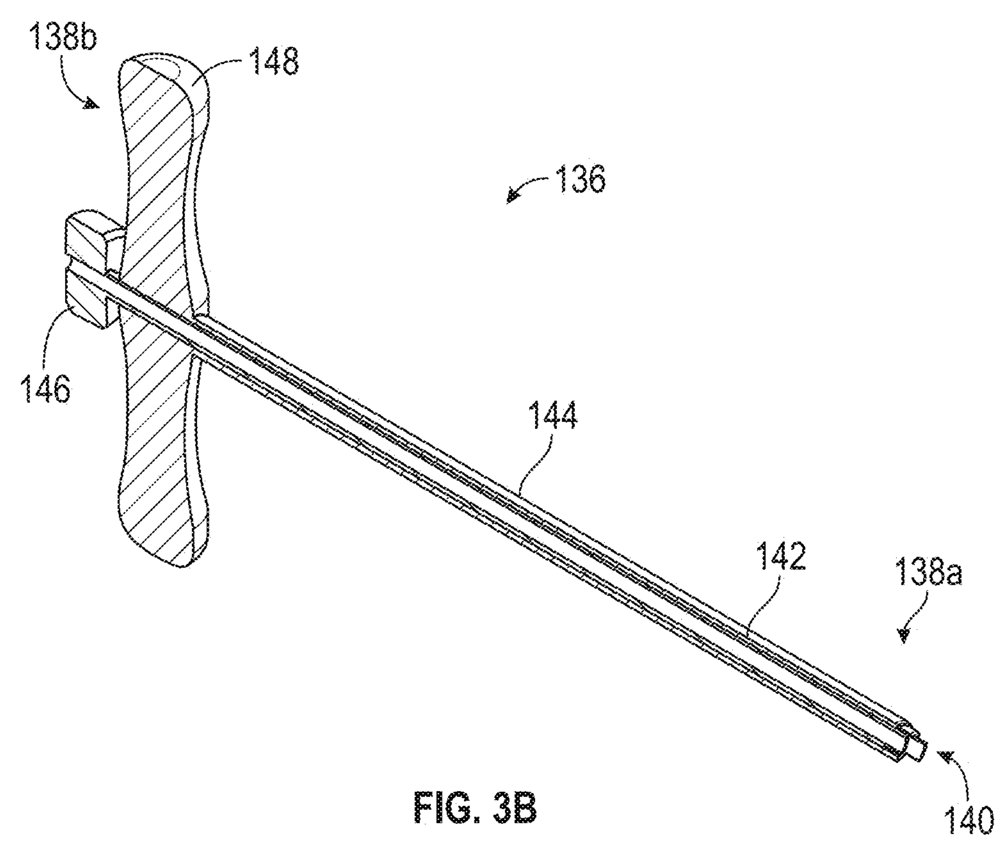
FIG. 3B illustrates a cross-sectional view of the insertion instrument for some embodiments.
Figure 3C:
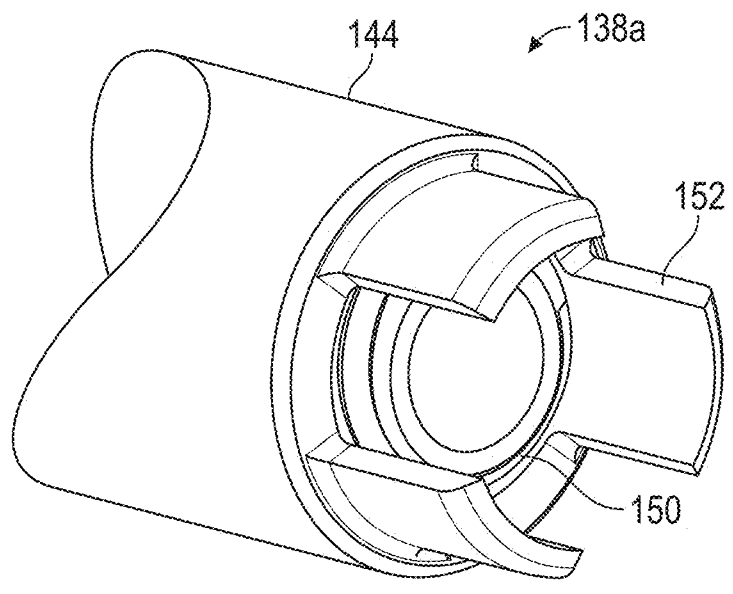
FIG. 3C illustrates a close-up view of a distal end of the insertion instrument for some embodiments.

In some embodiments, implant 108 is post-processed after printing via hot isostatic pressing. Other post-processing steps, such as heat treatment, machining, surface treatments (e.g., roughening), and the like may be performed. For example, in some embodiments, at least a portion of implant 108 may undergo a roughening treatment. Providing a roughened surface may promote bone ingrowth of implant 108. INSERTION INSTRUMENTS AND SURGICAL TOOLS FIGS. 3A and 3B illustrate a perspective view and a cross-sectional view, respectively, of an insertion instrument 136 for some embodiments of the present disclosure. FIG. 3C illustrates a close-up view of a distal end of the insertion instrument 136 for some embodiments. Once the SI joint 102 is prepared for insertion of implant 108 (discussed further below), insertion instrument 136 may be used to insert implant 108 into SI joint 102.

Insertion instrument 136 may comprise a distal end 138*a* for coupling to implant 108 and a proximal end 138*b* for the operator to interface with insertion instrument 136. A bore 140 may extend lengthwise through insertion instrument 136. The bore 140 may provide a path for inserting insertion instrument 136 over a guidewire (FIGS. 8A-8B) during the insertion process, as discussed further below.

Insertion instrument 136 may further comprise a rod 142 that may be received within a shaft 144. Rod 142 and shaft 144 may be concentric. An inner surface of shaft 144 may abut an outer surface of rod 142. A rod handle 146 may be coupled to a proximal end of the rod 142, and a shaft handle 148 may be coupled to the shaft 144. Shaft handle 148 may comprise a bore through which shaft 144 may extend such that a portion of shaft 144 extends proximally from shaft handle 148. In some embodiments, a proximal face of shaft handle 148 coincides with a proximal face of shaft 144. In some embodiments, rod 142 is movable longitudinally within shaft 144. The travel distance of rod 142 in the distal direction may be limited by a proximal face of shaft handle 148.

As shown in FIG. 3C, a distal end of rod 142 may comprise external threads 150 configured to threadedly engage with internal threads 124 on proximal section 110*b*. A distal end of shaft 144 may comprise prongs 152 configured to engage with recesses 126 in proximal section 110*b*. An operator may rotate rod handle 146 to mate external threads 150 with internal threads 124. Once engaged, prongs 152 may be inserted into recesses 126 to complete the coupling of insertion instrument 136 with implant 108. When implant 108 is coupled to insertion instrument 136, the operator may use shaft handle 148 to rotate insertion instrument 136, thereby driving implant 108 into SI joint 102. The flutes 122 and/or threads 112 may self-drill implant 108 into SI joint 102.

Figure 4A:
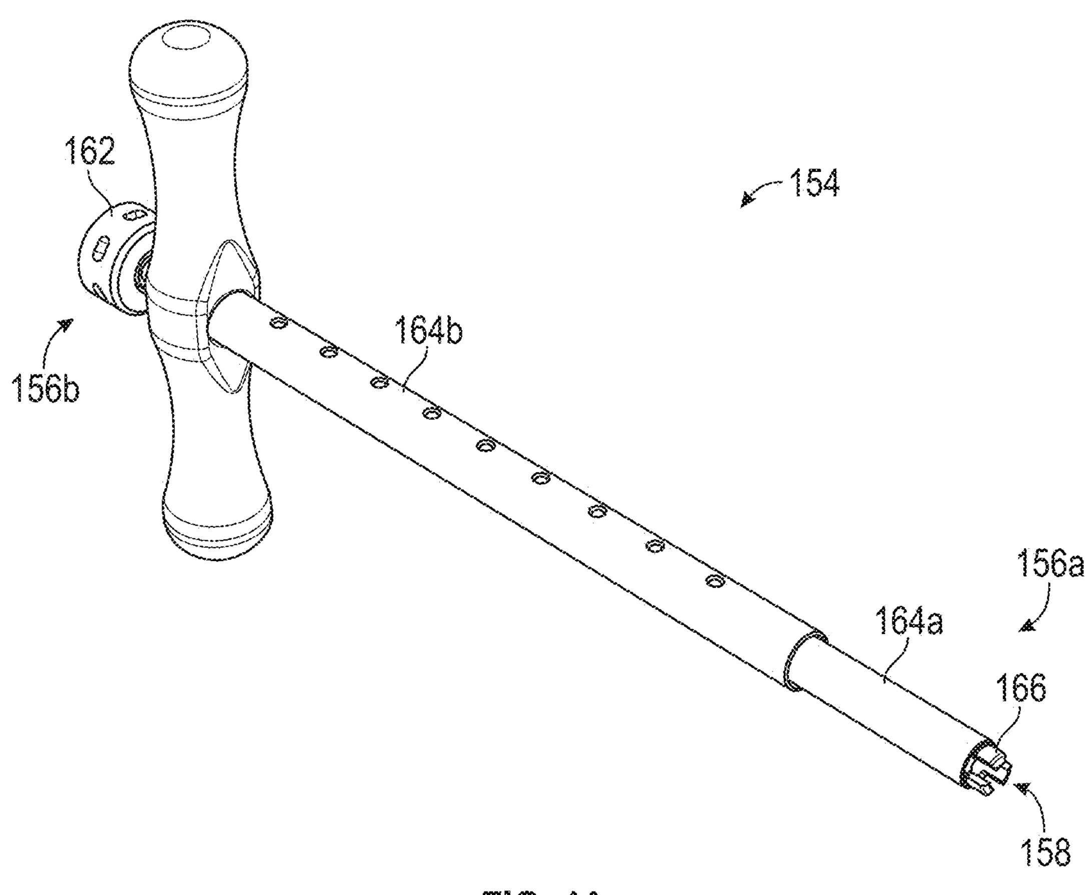
FIGS. 4A and 4B illustrate a second insertion instrument for some embodiments.
Figure 4B:
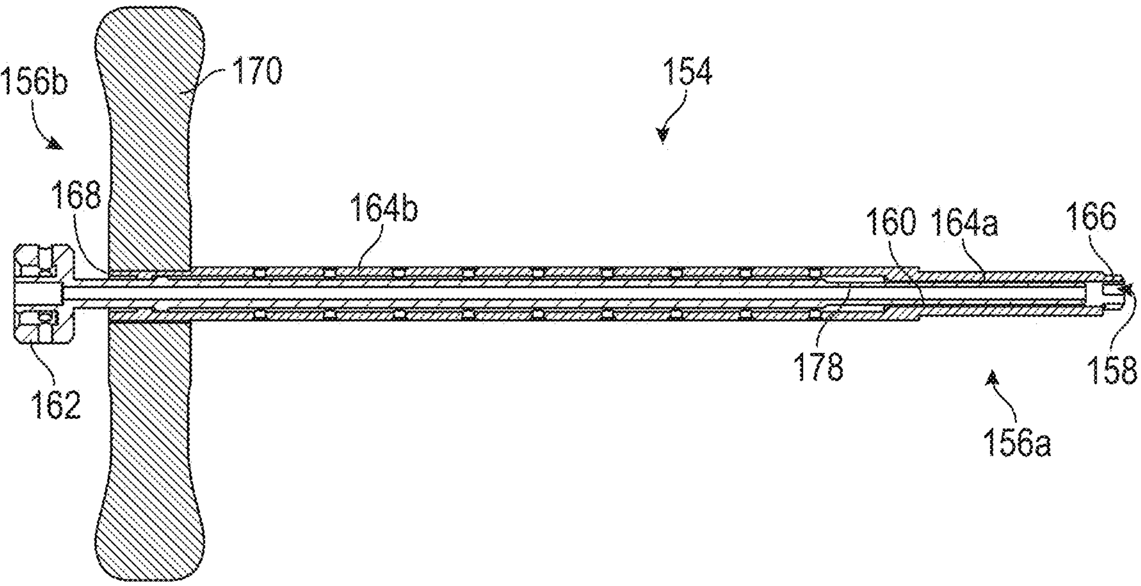

FIGS. 4A and 4B illustrate a second insertion instrument 154 in accordance with embodiments of the present disclosure. The second insertion instrument 154 may be substantially similar to the first insertion instrument 136 described above. In some embodiments, the insertion instrument 154 is configured to couple to a syringe or other bone graft delivery device for delivering bone graft down the cannula of the second insertion instrument 154 and to the implant 108, which advantageously may be done while the implant 108 is in the implantation site.

Second insertion instrument 154 may comprise a distal end 156*a* for coupling to implant 108 and a proximal end 156*b* for the operator to interface with the insertion instrument 154. A cannula or bore 158 may extend lengthwise through the insertion instrument 154. The bore 158 may provide a passageway for inserting insertion instrument 154 over a guidewire as described above. Enabling the implant 108 to be placed over the guidewire eases the insertion of the implant 108 into the patient as the guidewire can guide the path into the SI joint 102.

Insertion instrument 154 may comprise a rod subassembly comprising a rod 160 and a knob 162; a shaft subassembly comprising a first shaft section 164*a* including prongs 166, and a second shaft section 164*b*, a bushing 168 received within second shaft section 164*b*; and a handle 170. The rod subassembly may be at least partially received within the shaft subassembly. Distal travel of rod 160 relative to the shaft subassembly may be limited by contact of knob 162 with a proximal surface of the handle 170. The rod subassembly and the shaft subassembly are discussed in further detail with respect to FIGS. 5A-5C and FIGS. 6A-6B, respectively.

Coupling of the insertion instrument 154 to the implant 108 may be substantially similar to the coupling of insertion instrument 136 to implant 108 discussed above. Specifically, the surgeon may (1) retract knob 162 proximally; (2) engage prongs 166 with recesses 126 on implant 108; (3) push knob 162 distally to expose a threaded distal end (see FIG. 5A) of the rod 160; and (4) rotate knob 162 to mate the threaded distal end of the rod 160 with internal threads 124 of implant 108. Once implant 108 is coupled to the insertion instrument 154, a syringe may be coupled to the proximal end of the rod 160, and bone graft may be delivered from the syringe, through the rod 160, and into the implant 108, which may be done at any point while the implant 108 and the insertion instrument 154 are coupled.

Figures 5A, 5B:
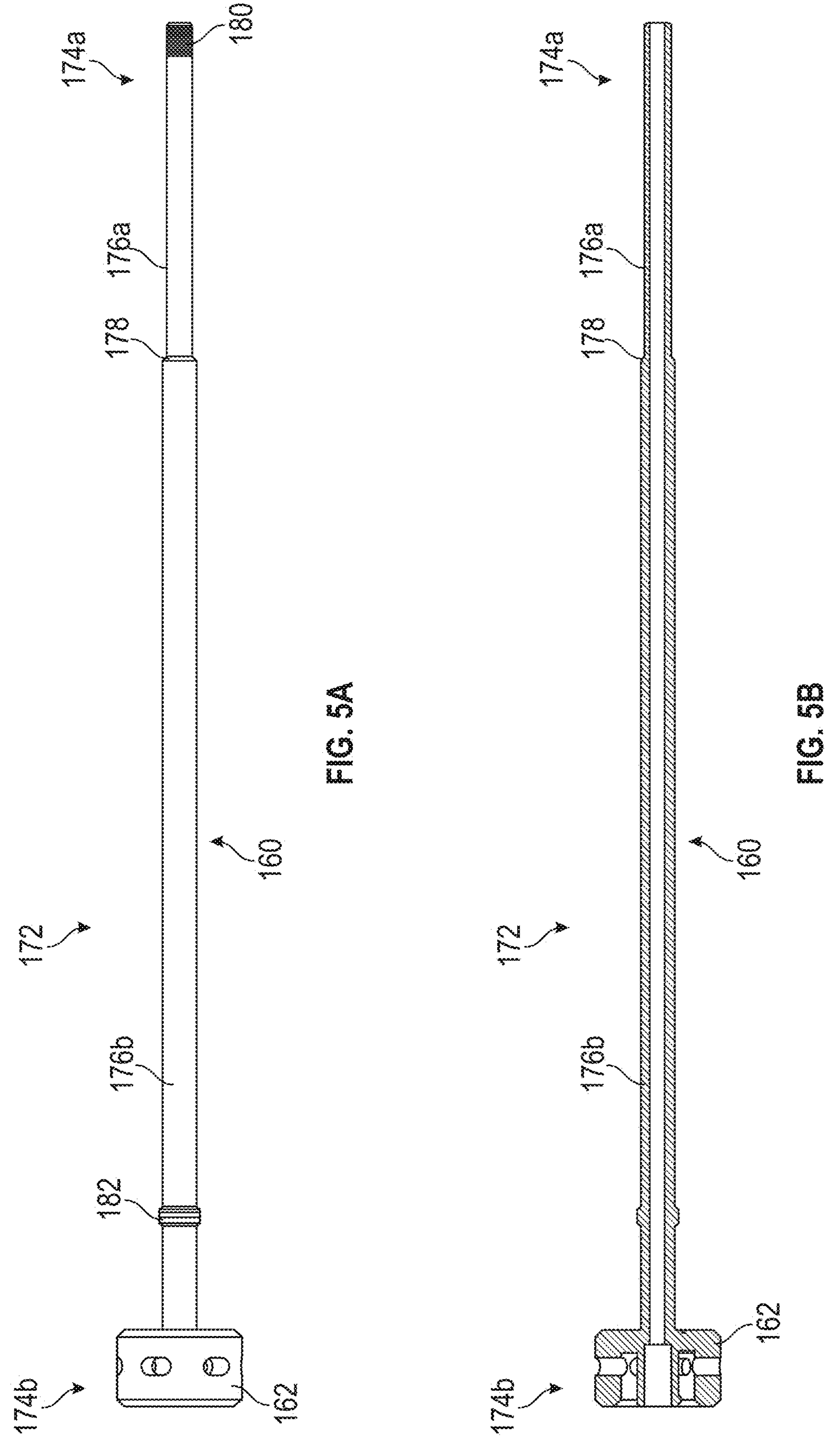
FIGS. 5A-5C illustrate a rod subassembly of the second insertion instrument for some embodiments.

Turning now to FIGS. 5A and 5B, a planar and cross-sectional view of the rod subassembly 172 of the insertion instrument 154 is depicted for some embodiments of the present disclosure. Rod subassembly 172 may include a distal end 174*a* and a proximal end 174*b*. Rod 160 may further include a first rod portion 176*a* and a second rod portion 176*b* separated by a shoulder 178. In some embodiments, rod 160 is unitary, while in other embodiments rod portions 176*a*, 176*b* may be distinct and coupled at shoulder 178 to form rod 160. First rod portion 176*a* may have a first, smaller diameter than second rod portion 176*b*. First rod portion 176*a* may include external threads 180 for threadedly engaging with internal threads 124. The external threads 180 may be at a distalmost end of rod 160.

Figure 6B:
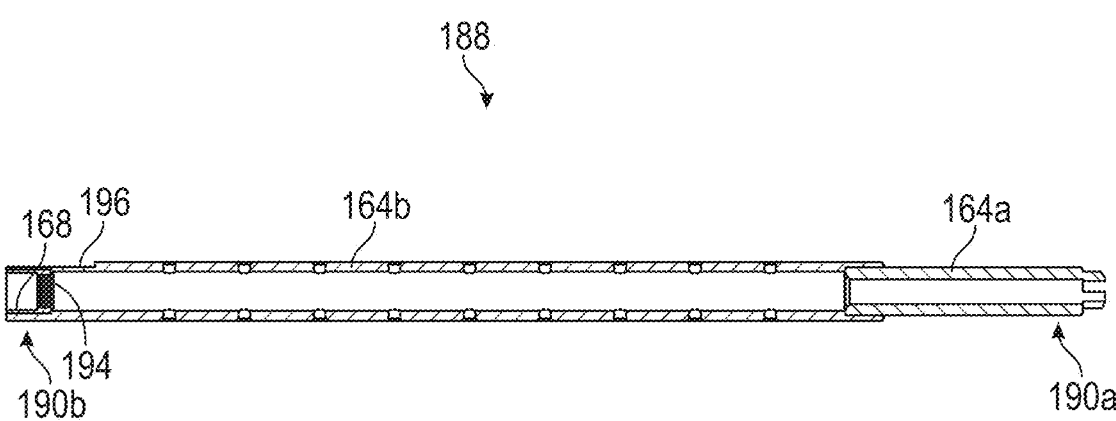

Second rod portion 176*b* may also include external threads 182 configured to threadedly engage with corresponding internal threads in second shaft section 164*b* (see FIG. 6B). The threaded engagement of the external threads 182 and the shaft threads may couple the rod subassembly 172 to the shaft subassembly. Without this coupling, rod 160 could fall out of the shaft subassembly, which may require cleaning and disinfection or replacement of the insertion instrument 154 if the rod 160 were to hit the ground or other non-sanitized surface. Therefore, providing a threaded coupling to couple the rod subassembly with the shaft subassembly may be advantageous. Additionally, the threaded coupling enables the surgeon to easily disengage the two subassemblies for cleaning purposes, for example.

Figures 5C, 6A:
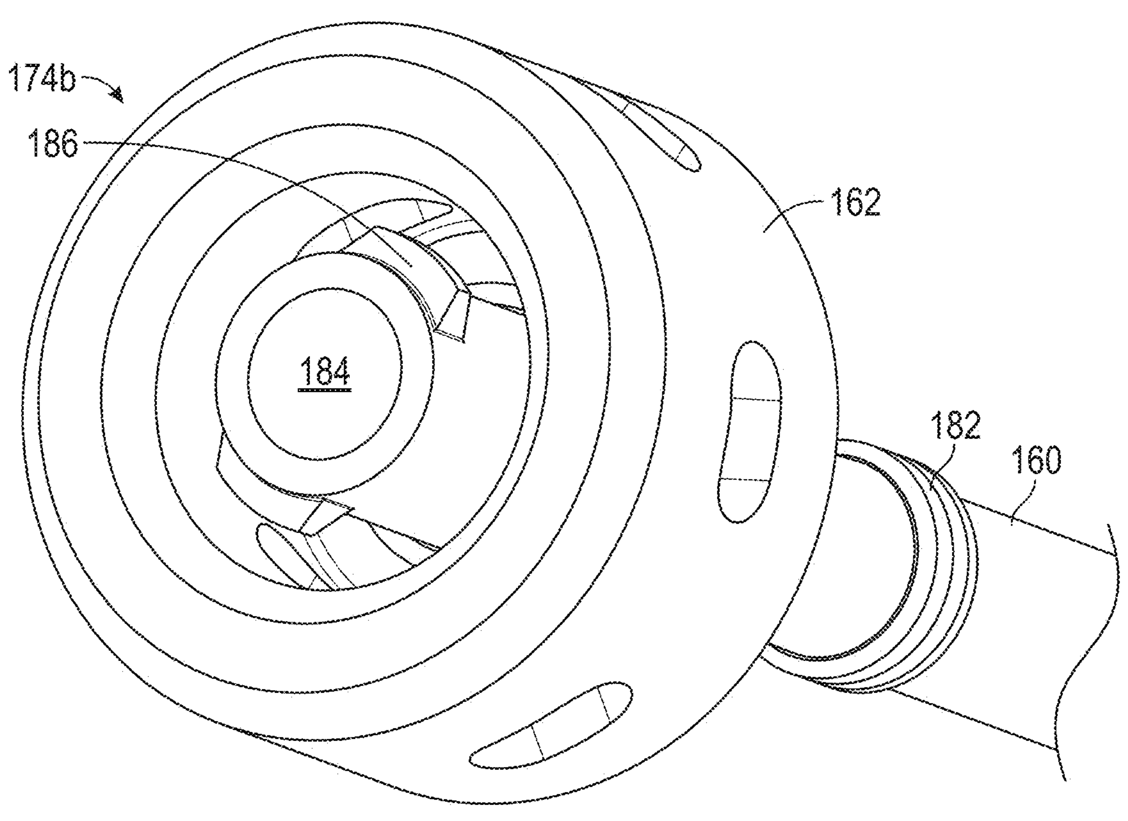
FIGS. 6A-6B illustrate a shaft subassembly of the second insertion instrument for some embodiments.

Turning now to FIG. 5C, a perspective view of proximal end 174*b* of rod subassembly 172 is illustrated in accordance with aspects of the present disclosure. As depicted, knob 162 includes an opening 184 therethrough via which a proximal end of rod 160 is accessible. In some embodiments, the proximal end of rod 160 is formed as a female luer lock 186. The luer lock 186 may provide a connecting point for coupling a syringe, other bone graft delivery device to rod 160, or intermediary male luer lock to rod 160 such that bone graft can be injected into implant 108 either when implant 108 is coupled to insertion instrument 154 and out of the patient, when implant 108 is coupled to insertion instrument 154 and within the patient, or both. As previously discussed, rod 160 may be cannulated via inclusion of bore 158. Accordingly, to fill implant 108 with bone graft, a surgeon may couple a syringe to rod 160 via luer lock 186 and push the bone graft through rod 160 and into implant 108 when implant 108 is coupled to insertion instrument 154.

Enabling post-filling of bone graft (i.e., filling after implant 108 is at the implantation site) may be advantageous for a number of reasons. First, by post-filling the implant 108, it may be ensured that the entirety of implant 108 can be fully filled with bone graft after placement. As previously discussed, implant 108 may be inserted over a guidewire. Placing the implant 108 over the guidewire may prevent the implant 108 from being entirely packed with bone graft due to the presence of the guidewire, along with the potential for bone graft to be forced out of the implant 108 as it travels over the guidewire. Therefore, post-filling of bone graft after removal of the guidewire allows for the implant 108 to be fully packed with bone graft. It should be noted the surgeon may both pre-fill the implant 108 with bone graft and post-fill the implant with bone graft, and by post-filling, any bone graft that was unable to be added due to the presence of the guidewire and/or comes out incidentally with removal of the guidewire can be replaced by post-filling as described herein. Additionally, by post-filling through insertion instrument 154 as opposed to another bone graft delivery device, the number of devices required for the surgery is reduced. Additionally, delivering bone graft via an insertion instrument makes it easier to fill the implant 108 with bone graft when in the patient because the insertion instrument 154 is already coupled to the implant 108. Thus, the surgeon merely needs to couple a syringe to the insertion instrument 154 via luer lock 186 rather than decoupling the insertion instrument 154 from the implant 108 and then coupling another bone graft delivery instrument to implant 108.

Looking now at FIGS. 6A and 6B, planar and cross-sectional views of a shaft subassembly 188 are depicted for some embodiments of the present disclosure. For clarity of illustration, handle 170 is not shown in FIGS. 6A-6B. Shaft subassembly 188 may include a distal end 190*a* and a proximal end 190*b*, along with first shaft section 164*a* and second shaft section 164*b* as discussed previously. As shown, a proximal end of first shaft section 164*a* is partially received within a distal end of second shaft section 164*b*. First shaft section 164*a* and second shaft section 164*b* may be coupled via welding, a press fit, a pinned connection, or by any other coupling means.

A proximal end of second shaft section 164*b* may be received within handle 170, and second shaft section 164*b* may be coupled to handle 170 via a weld, a press fit, a threaded connection, a pinned connection or the like. Additionally, within second shaft section 164*b*, bushing 168 may be received. Bushing 168 may comprise internal threads 194 for coupling to external threads 182. The threaded connection between internal threads 194 and external threads 182 may lock movement of rod 160 relative to shaft subassembly 188. When the surgeon wishes to move rod 160 distally (e.g., to engage prongs 166 with internal threads 124), the surgeon may rotate knob 162 to unthread rod 160 from second shaft section 164*b*. Likewise, the surgeon may rotate knob 162 to move rod 160 proximally to disconnect the rod subassembly 172 from the shaft subassembly 188.

As shown in FIG. 6A, a proximal end of second shaft section 164*b* may have a flat surface 196 such that the proximal end is configured as a D shaft, thereby providing an anti-rotation feature when coupled to handle 170, which may have a corresponding flat within the opening through which second shaft section 164*b* is received.

In some embodiments, insertion instrument 136, 154 comprises titanium or a titanium alloy. In some embodiments, insertion instrument 136, 154 comprises stainless steel. In some embodiments, insertion instrument 136, 154 comprises a polymer, a plastic, a bioabsorbable material, or any combination thereof. For example, insertion instrument insertion instrument 136, 154 may be formed from polyacrylamide or IXEFR. In some embodiments, insertion instrument 136, 154 is additively manufactured and may be formed from RULON, PEEK, or the like. In some embodiments, at least a portion of insertion instrument 136, 154 is radiopaque or radiolucent. In some embodiments, insertion instrument 136, 154 is disposable.

In some embodiments, one or more components of insertion instrument 136, 154 are coated in a biocompatible, corrosion resistant material to help protect and/or strengthen the component. For example, some or all portions of insertion instrument 136, 154 may be advantageously reinforced with a coating material to increase the durability of the components while maintaining safety to the patient by the coating material being of a biocompatible substance. Such a coating material may be applied specifically to components of insertion instrument 136, 154 that come into contact with tissue of the patient. In some embodiments, the coating material may be an anodized metal. In some embodiments, the coating material may be formed by an electroplating process, such as a hard chromium electroplating process. For example, in some embodiments, the coating material may be MEDCOAT 700™. In some embodiments, the thickness of the coating material may be between about 1 μm to about 15 μm. In some embodiments, the coating material may be between about 2 μm to about 10 μm.

Figure 7:
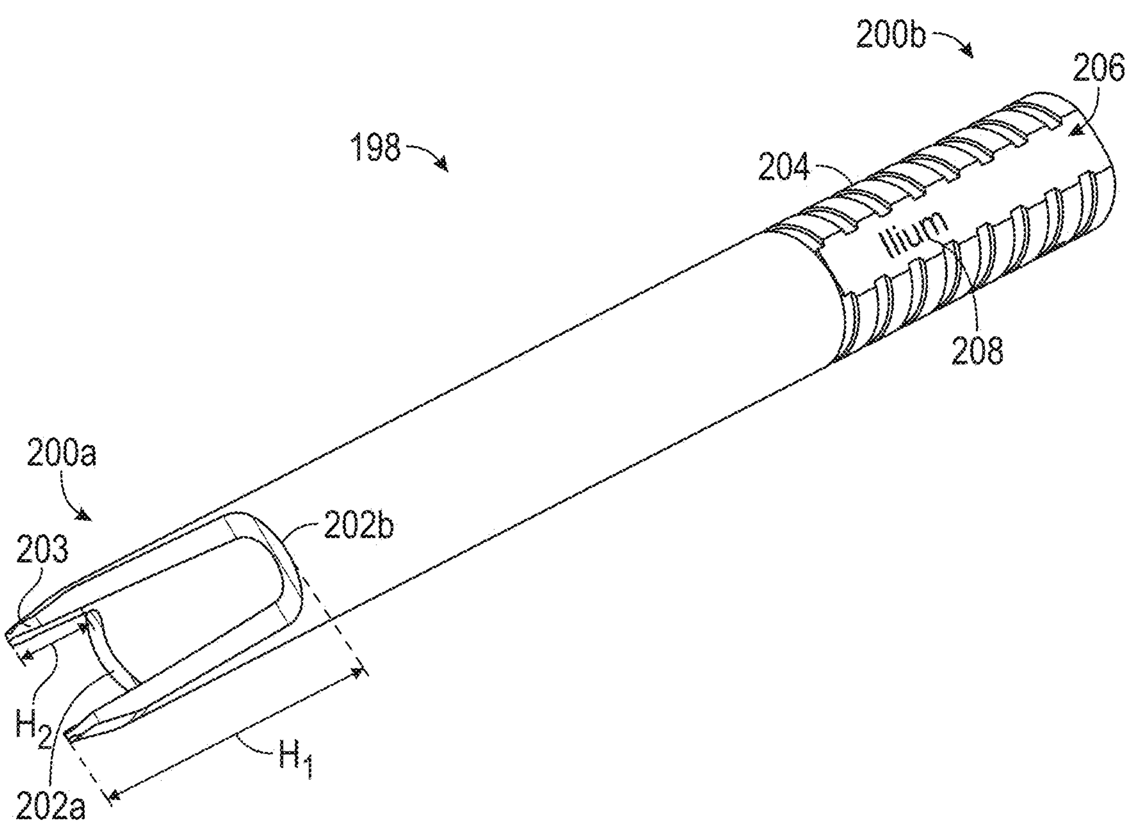
FIG. 7 illustrates a joint sleeve configured to be inserted into the sacroiliac joint for some embodiments.

FIG. 7 illustrates a joint sleeve 198 in accordance with embodiments of the present disclosure. Joint sleeve 198 may be inserted into the patient for soft tissue dilation, prior to insertion of the insertion instrument 136, 154, and may provide a pathway for the surgeon to insert the insertion instrument 136, 154, and the implant 108.

Joint sleeve 198 may have a distal end 200*a* and a proximal end 200*b*. Distal end 200*a* may comprise a first shoulder 202*a* opposite a second shoulder 202*b* and include prongs 203. Shoulders 202*a*, 202*b* may be configured to dock against the sacrum and the ilium. Second shoulder 202*b* may have a height H1 that is larger than a height H2 of the first shoulder 202*a*. The heights H1, H2 may be selected to correspond to where joint sleeve 198 will contact the sacrum and ilium when placed in the correct position within the patient. The shorter shoulder may align with the sacrum and the larger shoulder with the ilium. Thus, the shoulders 202*a*, 202*b* may provide an indication to the surgeon when they have correctly placed the joint sleeve 198. When in the final position, the prongs 203 may abut the inner cortical walls of each of the sacrum and the ilium that form the boundaries of the SI joint space.

Proximal end 200*b* may include a ridged or textured surface 204 for the surgeon to grip when using joint sleeve 198. The ridged surface 204 may extend around a circumference of proximal end 200*b* but may be bisected by two flat sections 206. Two flat sections 206 may be aligned with shoulders 202*a*, 202*b*. The flat sections 206 may include indicators 208 indicating which bone the corresponding shoulder 202*a*, 202*b* should dock against. As shown, the indicator 208 is labeled "ilium", and a second indicator (not shown) on the opposite side of the sacrum indicator 208 would be labeled "sacrum."

Figure 8A:
FIGS. 8A and 8B illustrate surgical kits for some embodiments.
Figure 8A:
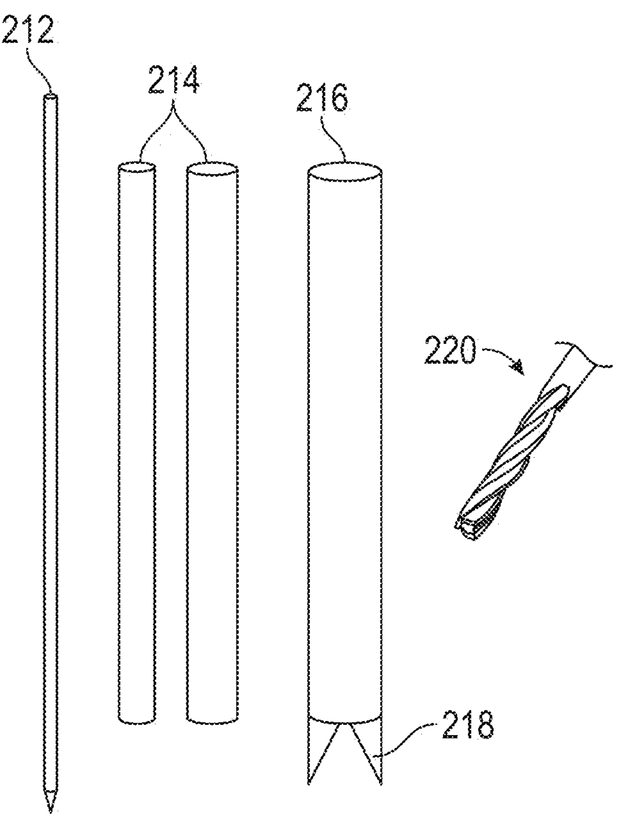

Turning now to FIG. 8A, an exemplary set of tools 210 is illustrated for preparing a target space (e.g., SI joint 102) for insertion of an implant 108 for some embodiments of the present disclosure. In some embodiments, one or more of exemplary tools 210 may be provided as part of a surgical kit along with implant 108 and/or insertion instrument 136 for bony fixation of a target space, such as SI joint 102.

In some embodiments, tools 210 comprises a guidewire 212. Guidewire 212 may be inserted into a minimally invasive incision and, under fluoroscopy, guidewire 212 may be advanced to locate the target space where it is desired to place implant 108. In some embodiments, tools 210 comprises one or more dilators 214. Dilators 214 may be hollow tubes that are placed over guidewire 212 to create a working channel for insertion of implant 108. Dilators 214 may be provided in increasing sizes such that a larger sized dilator 214 may be placed over a smaller-sized dilator to dilate the target space.

In some embodiments, tools 210 comprises a final dilator 216. Final dilator 216 may correspond to joint sleeve 198 described above. The final dilator may have a larger size than dilators 214 such that final dilator 216 may be placed over the largest dilator 214. Additionally, in some embodiments, the final dilator 216 may have prongs or tangs 218 corresponding to prongs 203 discussed above. The tangs 218 may be configured to dock into the SI joint 102. For example, a first tang 218 may engage with the ilium 104 and a second tang 218 may engage with the sacrum 106. Docking tangs 218 with ilium 104 and/or sacrum 106 may provide positive feedback to the surgeon to indicate that SI joint 102 was correctly located. Final dilator 216 may also provide further distraction to SI joint 102 to prepare SI joint 102 for implantation of implant 108. Through final dilator 216, implant 108 and insertion instrument 136 may be inserted when implanting implant 108. In some embodiments, final dilator 216 comprises at least one tang 218. In some embodiments, final dilator 216 comprises two or more tangs 218. In some embodiments, tangs 218 are wedge shaped. Other shapes are within the scope hereof. Generally, final dilator 216 may have a distal end that is configured for engaging with bone such that final dilator 216 can dock into the target space. Providing a final dilator 216 as discussed herein may be advantageous in correctly locating SI joint 102, which may be difficult from a posterior approach due to the irregular shape of the joint that makes the joint difficult to view under fluoroscopy. Accordingly, with the positive feedback provided by final dilator 216, the surgeon may be assured that the correct location for inserting implant 108 has been located.

In some embodiments, tools 210 comprises a drill bit 220. Drill bit 220 may be used for drilling a pilot hole to access the target space. In some embodiments, drill bit 220 is cannulated, as shown, such that drill bit 220 may be inserted over guidewire 212. In some embodiments, tools 210 further comprises a decorticator (not shown) for roughening the target space. The decorticator may likewise be cannulated for insertion over guidewire 212. It will be appreciated that various other tools may be provided with a surgical kit for bony fusion without departing from the scope hereof. For example, in some embodiments, implant 108 may be used with a bone plate through which one or more implants 108 may be inserted for bony fusion (see e.g., FIG. 10B).

Figure 8B:
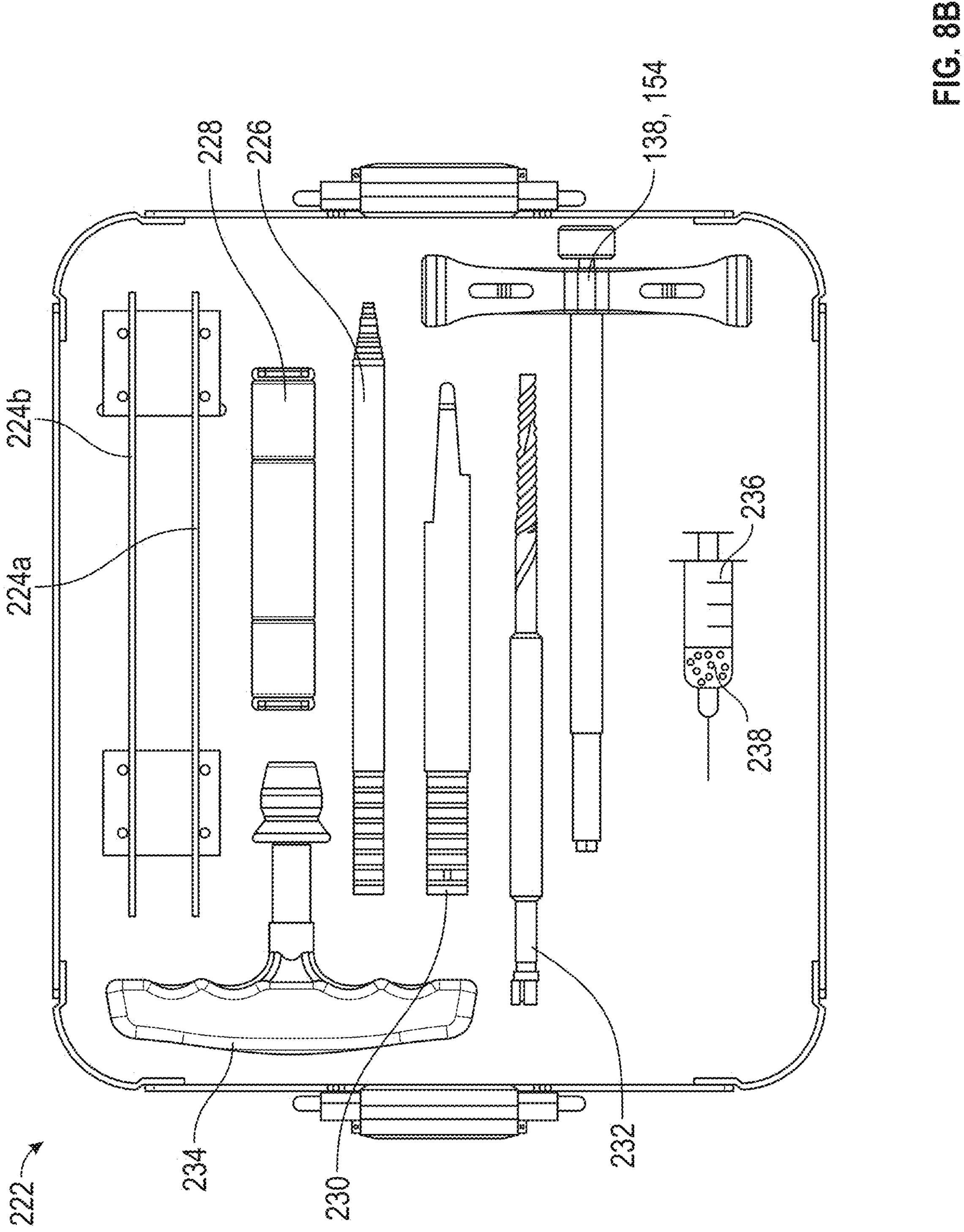

An exemplary surgical kit 222 is depicted in FIG. 8B in accordance with embodiments of the present disclosure. Surgical kit 222 may include any of the tools described above with respect to FIG. 8A. Surgical kit 222 may include a first guidewire 224*a* and a second guidewire 224*b*. First guidewire 224*a* may be a trocar guidewire and may correspond to guidewire 212 discussed above. Second guidewire 224*b* may be a blunt guidewire. Either of the guidewires 224*a*, 224*b* may be used by the surgeon to access the SI joint. When in the final position, a distal tip of the guidewire 224*a*, 224*b* may be between the S1 and S2 foramen.

Surgical kit 222 may further include a joint finder 226 that may be used to locate the SI joint. The joint finder 226 may be cannulated such that the joint finder 226 can be placed over the guidewire 224*a*, 224*b*. Additionally, a distal end of the joint finder 226 may be tapered. The tapered end may be inserted by the surgeon into the SI joint and the transition point of the tapered end where the diameter of the tapered end transitions to become the diameter of the remaining length of the joint finder 226 may serve as an indicator of where the surgeon should stop further advancement of the joint finder 226. To state another way, the surgeon may insert the joint finder 226 into the SI joint 102 and use the position at which the largest diameter of the joint finder 226 is going to enter the SI joint space as the indicator that further advancement of the joint finder 226 should cease. An impactor 228 may be provided that the surgeon may strike with a mallet (not shown) to advance the joint finder 226 into the joint space.

Surgical kit 222 may also include a joint sleeve 230 corresponding to joint sleeve 198 discussed above. Joint sleeve 230 may be inserted over joint finder 226 and docked against the sacrum and the ilium. Once joint sleeve 230 in the correct position, joint finder 226 may be retracted, leaving an opening through which the insertion instrument 136, 154 and other tools may be inserted.

With joint sleeve 230 in place, the surgeon may use a decorticator 232, which may be driven by a T-handle 234. The decorticator 232 may have a distal end configured as a drill bit, and the surgeon may hand drill the decorticator 232 into the SI joint space. In some embodiments, the decorticator 232 has a thread sizing that is the same as the threads 112 on implant 108 such that implant 108 can follow the thread path created by decorticator 232. As with the joint finder 226 and the joint sleeve 230, the decorticator 232 may be cannulated such that the decorticator 232 is insertable over the guidewire 224*a*, 224*b*.

Surgical kit 222 may further include a syringe 236 and bone graft 238. Syringe 236 may include a male luer lock or may be configured to couple to a male luer lock such that syringe 236 can be coupled to luer lock 186 on rod 160. When syringe 236 is coupled to rod 160 and implant 108 is also coupled to rod 160, syringe 236 becomes fluidly coupled to implant 108. Accordingly, bone graft 238 may be loaded into syringe 236, and syringe 236 may be coupled to rod 160 via luer lock 186 such that bone graft 238 may be delivered into implant 108. As discussed above, filling implant 108 with bone graft 238 may be advantageous at least because implant 108 may be easier to insert/thread into the SI joint space when implant 108 is not filled with bone graft 238; however, it is desirable to pack implant 108 with bone graft to promote bony fusion. Thus, post-filling of implant 108 is desirable.

Implant Insertion Method

Figure 9:
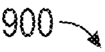
FIG. 9 illustrates an operational method for inserting the implant for some embodiments.
Figure 9:
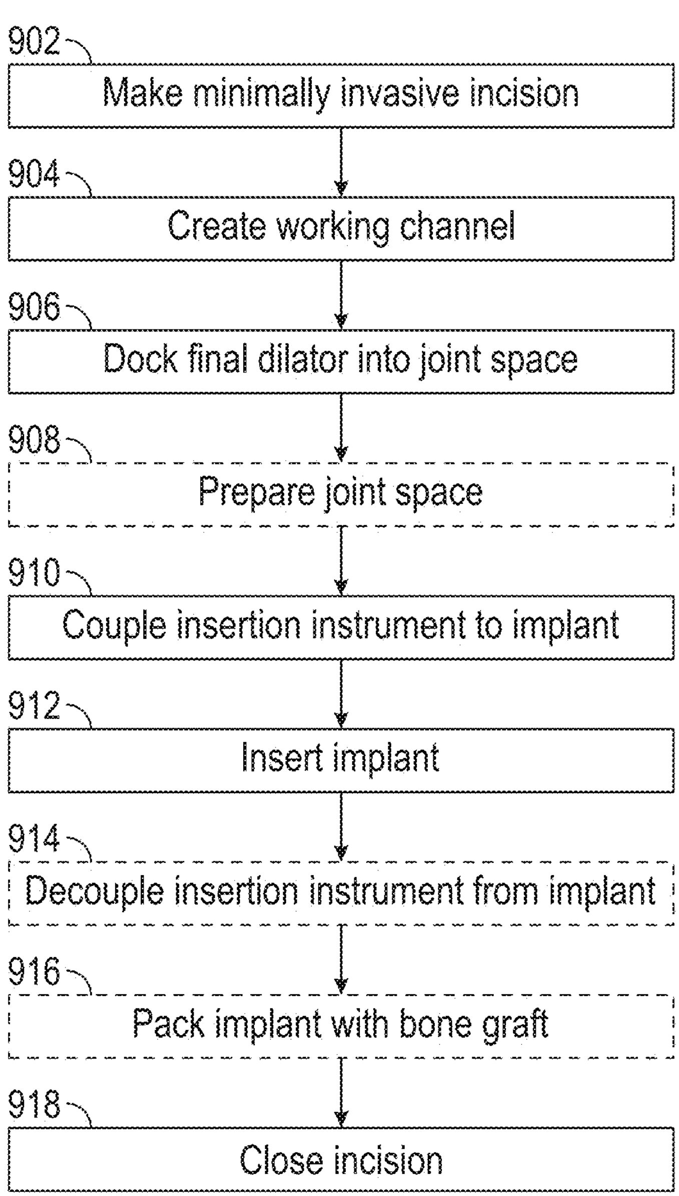

FIG. 9 illustrates a method 900 for inserting implant 108 into SI joint 102 in accordance with embodiments of the present disclosure. One or more implants 108 may be inserted into the SI joint 102 to provide fusion and stabilization thereof. In some embodiments, the implant 108 is inserted at the S1 level of the spine. Placement of the implants 108 may be done to avoid damaging the neuroforamen that are medial from the sacrum 106. While method 900 is discussed with respect to a posterior approach, one of skill in the art will appreciate that method 900 may be suitably modified to insert implant 108 via other approaches, such as anteriorly.

Method 900 may begin at step 902 where a minimally invasive incision may be made on the patient. As described above, minimally invasive incisions reduce blood loss, recovery time, and hospital stay, among other benefits, as compared to open surgery. However, it is contemplated that embodiments herein may be practiced in an open surgery without departing from the scope hereof. In some embodiments, the minimally invasive incision is made to provide posterior access to SI joint 102 such that implant 108 may be inserted into SI joint 102 via a posterior approach as discussed with respect to FIG. 1. The patient may be placed in a prone position to provide posterior access to SI joint 102. In some embodiments, a separate incision is made for each implant 108 inserted into the SI joint 102. In some embodiments, a single incision is made for inserting implant 108 into SI joint 102. In some embodiments, one, two, three or more implants 108 may be inserted into SI joint 102.

Next, at step 904, a working channel for inserting the implant 108 may be created. In some embodiments, the working channel is created by successively inserting one or more dilators 214 over a guidewire 212, 224*a*, 224*b* that is inserted into SI joint 102 to dilate soft tissues surrounding SI joint 102. In embodiments where multiple implants 108 are inserted, a parallel pin guidewire tool may be used to insert a guidewire 212 for each implant 108. The guidewires 212, 224*a*, 224*b* may be inserted by tapping or any other method as will be appreciated by one of skill in the art. In some embodiments, a joint finder 226 is provided that is inserted over a guidewire 212 for locating the SI joint space as discussed above.

Thereafter, at step 906, final dilator 216 or joint sleeve 198 may be inserted. The final dilator 216 may comprise tangs, prongs, or other engaging features that may dock into SI joint 102 (e.g., prongs 203). The dilators 214, 216 may be tubes or other hollow bodies that provide a pathway for inserting implant 108 and insertion instrument 136 therein to access SI joint 102. In some embodiments, step 906 comprises inserting only joint sleeve 198 and no other sleeves or dilators are inserted. The dilators 214, 216 or joint sleeve 198 may be inserted over the guidewire 212, 224*a*, 224*b* and over the joint finder 226.

At optional step 908, one or more site preparation steps may be taken to prepare SI joint 102 for insertion of implant 108. In some embodiments, SI joint 102 may be roughened using a cannulated decorticator or other like tool, such as decorticator 232. Another preparation step may comprise drilling a pilot hole to access SI joint 102, which may be done using drill bit 220. In some embodiments, decorticator 232 is configured both to drill a pilot hole and to decorticate the SI joint space, e.g., by having a self-drilling tip. As described above, distal section 110*a* may be configured to self-drill implant 108 into SI joint 102 such that drilling a pilot hole may be unnecessary.

Next, at step 910, with SI joint 102 prepared for insertion of implant 108, implant 108 may be coupled to an insertion instrument 136, 154. As described above, external threads 150, 180 on rod 142, 160 may couple to internal threads 124 in proximal section 110*b* and prongs 152, 166 on shaft 144, 188 may couple to recesses 126 in proximal section 110*b*. Threadedly engaging external threads 150, 180 with internal threads 124 may lock implant 108 to insertion instrument 136, 154, while the engagement between prongs 152, 166 and recesses 126 may allow for the rotational movement of insertion instrument 136, 154 to rotate implant 108. Implant 108 may also be pre-filled with bone as previously discussed.

Next, at step 912, implant 108 may be inserted into SI joint 102 by rotationally driving insertion instrument 136, 154 via shaft handle 148, 170. As implant 108 is advanced distally, flutes 122 and/or threads 112 may work to self-drill implant 108 into SI joint 102. As discussed above, the procedure may be conducted under fluoroscopy such that the surgeon may monitor the position of implant 108 during insertion. When in the final position, threads 112 may be engaged with ilium 104 and sacrum 106, and this threaded engagement may mitigate movement of implant 108 once implanted. Furthermore, heels 114 may engage with ilium 104 and sacrum 106 to prevent backing out of implant 108 from SI joint 102. The final position of the implant 108 may be from the posterior-inferior aspect of the articular portion of the joint 102, anterior to the posterior superior iliac spine (PSIS), and posterior to the posterior inferior iliac spine (PIIS), ranging from 0 to 10 mm from the proximal end of SI joint 102.

Thereafter, at step 914, insertion instrument 136 may be decoupled from implant 108. Decoupling insertion instrument 136 from implant 108 may comprise unthreading external threads 150 from internal threads 124 and pulling insertion instrument 136 proximally to disengage prongs 152 from recesses 126. In some embodiments, step 914 is optional.

Next, at optional step 916, implant 108 may be packed with bone graft 238. The bone graft may be autograft, allograft, a synthetic bone graft, or the like. Bone graft may be inserted via cannula 118 and flow through openings 130 and into lattice structure 128. Because insertion instrument 136 is also cannulated, the bone graft 238 may be inserted through bore 140 and into cannula 118 when insertion instrument 136, 154 is coupled to implant 108. Thus, in some embodiments, step 916 occurs before step 914. In some embodiments, step 916 occurs before step 912, after the implant 108 is coupled to the insertion instrument 136, 154 and before insertion into the patient.

Insertion of bone graft 238 into implant 108 may involve coupling a syringe 236 to an insertion instrument 136, 154 via a luer lock 186 located at the proximal end of the rod 142, 160. Alternatively, or additionally, the bone graft 238 may be packed by hand by the surgeon. As described above, the open architecture of implant 108 may improve bone ingrowth because the bone graft may flow within the openings of implant 108. Accordingly, more bone graft may be added to implant 108 than prior implants. Implant 108 may also have bone graft packed to the exterior thereof. Lastly, at step 918, the incision may be closed to complete the insertion process.

While method 900 is discussed with respect to inserting implant 108 into SI joint 102, it will be appreciated that method 900 may be suitably modified for insertion of implant 108 at other locations in the body, such as the foot, ankle, shoulder, face, etc. For these operations, a posterior approach may not be taken, and embodiments of the present disclosure should not be construed as limited to only posterior approaches. Generally, a method for inserting implant 108 may comprise: (1) providing access to the target space (e.g., via an incision and subsequent dilations, etc.); (2) coupling implant 108 to insertion instrument 136; (3) inserting implant 108 with insertion instrument 136; and (4) performing any post-insertion steps (e.g., post-filling of bone graft, etc.).

In some embodiments, the above-described method 900 may be provided as instructions with a surgical kit. For example, the surgical kit may comprise the instrumentation required to perform the surgery, such as one or more implants 108, insertion instrument 136, and tools 210. The surgical kit may provide multiple sizes of the tools, implants 108, and inserter instruments 136, which may be selected based on the size of the patient. The surgeon may use the surgical kit to perform the fusions and follow the above-described method to carry out the operations. In some embodiments, the surgical kit is surgical kit 222.

Exemplary Implantation Sites

Figures 10A, 10B:
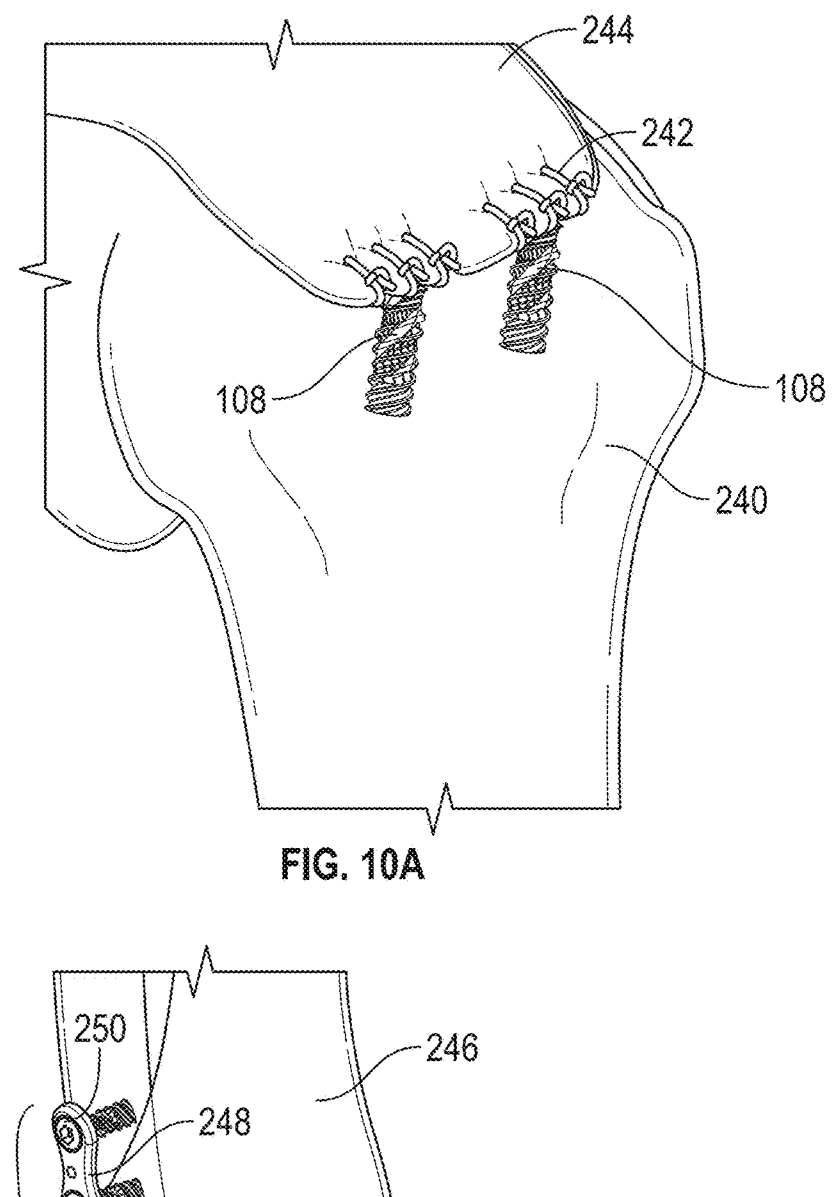
FIG. 10A illustrates an exemplary embodiment of the implant inserted in the rotator cuff for some embodiments.
FIG. 10B illustrates an exemplary embodiment of the implant inserted in the ankle for some embodiments.

FIGS. 10A and 10B illustrate exemplary use cases of implant 108 in other regions of the body in accordance with embodiments of the present disclosure. Looking first at FIG. 10A, implant 108 is shown for use in repairing a rotator cuff for some embodiments. Here, implant 108 may function as an anchor commonly used in rotator cuff repair. One or more implants 108 may be placed into the humerus 240. Implant 108 may be configured with suture strands 242 that can be passed through the tendon 244 as will be appreciated by one of skill in the art. The open architecture of implant 108, along with additively manufacturing implant 108 from a titanium alloy, may be advantageous over prior anchors.

Looking now at FIG. 10B, implant 108 is depicted inserted into an ankle 246 for some embodiments of the present disclosure. As shown, a plurality of implants 108 are inserted through a bone plate 248. Further, it is contemplated that each implant 108 may be formed with a head 250 (e.g., a screw head) for retaining implant 108 in bone plate 248. It is contemplated that implant 108 may be used with a bone plate 248 at various regions of the body. Generally, implant 108 may be useful with any bony structure that requires fusion and/or stabilization.

Features described above as well as those claimed below may be combined in various ways without departing from the scope hereof. The following examples illustrate some possible, non-limiting combinations:

(A1) An implant for bony fusion at a target space, comprising: a plurality of external threads extending along a length of the implant; a cannula extending along a longitudinal axis of the implant; a distal section; a proximal section configured to be coupled to an insertion instrument; and a central section between the proximal section and the distal section, the central section comprising: an interior core region adjacent to the cannula; a lattice structure located laterally between the interior core region and a minor diameter of the plurality of external threads; and a plurality of openings extending through the interior core region, the plurality of openings connecting the lattice structure to the cannula.

(A2) For the implant denoted as (A2), wherein the implant is configured to be packed with bone graft, and wherein the plurality of openings is connected to the lattice structure such that the bone graft flows between the plurality of openings and the lattice structure.

(A3) For the implant denoted as (A1) or (A2), wherein the distal section comprises at least one cutting flute for self-drilling the implant into the target space.

(A4) For the implant denoted as any of (A1) through (A3), wherein the proximal section comprises internal threading for threadedly engaging the insertion instrument, wherein rotation of the insertion instrument rotates the implant for insertion into the target space.

(A5) For the implant denoted as any of (A1) through (A4), wherein at least a portion of the plurality of external threads comprises at least one thread heel configured to reduce proximal movement of the implant when inserted into the target space.

(A6) For the implant denoted as any of (A1) through (A5), wherein the at least one thread heel is oriented in a first direction to prevent interference with threading of the implant during insertion.

(A7) For the implant denoted as any (A1) through (A6), wherein the central section comprises a length of about 30% to about 60% of the length of the implant.

(A8) For the implant denoted as any of (A1) through (A7), wherein the implant is formed from at least one of: a titanium alloy, stainless steel, magnesium, a polymer, a bioresorbable material, or an allograft, and wherein the implant is coated with hydroxyapatite.

(B1) An implant for bony fusion of a target space, comprising: a cannula along a longitudinal axis of the implant; a distal section configured to self-drill the implant into bone; a proximal section; and a central section between the distal section and the proximal section, comprising: a lattice structure fluidly connected to the cannula, wherein the lattice structure is configured to receive bone graft for bone ingrowth of the implant, wherein the implant comprises a plurality of external threads extending along a length of the implant.

(B2) For the implant denoted as (B1), wherein the central section further comprises: a core region adjacent to the cannula, and a plurality of fenestrations extending through the core region to fluidly connect the cannula to the lattice structure.

(B3) For the implant denoted as (B1) or (B2), wherein the lattice structure extends laterally from a perimeter of the core region to a minor diameter of the plurality of external threads.

(B4) For the implant denoted as any of (B1) through (B3), wherein the plurality of fenestrations follows a thread path of the plurality of external threads.

(B5) For the implant denoted as any of (B1) through (B4), wherein the implant comprises a variable diameter that increases from the distal section to the proximal section.

(B6) For the implant denoted as any of (B1) through (B5), wherein the target space is a sacroiliac joint, and wherein the plurality of external threads of the implant is configured to embed into a sacrum and an ilium of the sacroiliac joint.

(B7) For the implant denoted as any of (B1) through (B6), wherein the implant is configured to be inserted into the sacroiliac joint via a posterior approach.

(B8) For the implant denoted as any of (B1) through (B7), wherein the distal section comprises a plurality of internal threads and a plurality of recesses configured for coupling to an insertion instrument.

(C1) A method for bony fusion of a target space, comprising: providing an implant having a cannula along a longitudinal axis, comprising: a plurality of external threads extending along a length of the implant; a distal section; a proximal section configured to be coupled to an insertion instrument; and a central section between the proximal section and the distal section, the central section comprising: an interior core region adjacent to the cannula; a lattice structure located laterally between the interior core region and a minor diameter of the plurality of external threads; and a plurality of openings extending through the interior core region, the plurality of openings connecting the lattice structure to the cannula; and providing instructions, the instructions comprising steps of: couple the implant to the insertion instrument; and insert the implant into the target space using the insertion instrument.

(C2) For the method denoted as (C1), wherein the instructions further comprise: make a minimally invasive incision; successively insert a series of dilators into the minimally invasive incision to create a working channel; and dock into the target space using a final dilator, the final dilator comprising at least one distal tang to engage with the target space.

(C3) For the method denoted as (C1) or (C2), wherein the distal section comprises cutting threads and flutes configured to self-drill the implant into the target space.

(C4) For the method denoted as any of (C1) through (C3), wherein the instructions further comprise: pack the implant with bone graft, wherein the bone graft flows from between the cannula, the plurality of openings, and the lattice structure.

Many different arrangements of the various components depicted, as well as components not shown, are possible without departing from the scope of the claims below. Embodiments of the present disclosure have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims. Although the present disclosure has been described with reference to the embodiments illustrated in the attached drawing figures, it is noted that equivalents may be employed, and substitutions made herein, without departing from the scope of the present disclosure as recited in the claims.

The invention claimed is:

1. An insertion system for inserting a posterior sacroiliac (SI) joint implant, comprising:
- a guidewire;
- an insertion instrument, comprising:
  - a cannulated rod configured to be inserted over the guidewire, the cannulated rod comprising:
    - a rod distal end comprising a first set of external threads for threadedly engaging with the posterior SI joint implant; and
    - a rod proximal end comprising a female luer lock,
    - wherein the female luer lock is configured to couple the insertion instrument to a syringe such that bone graft is insertable into the posterior SI joint implant by the syringe and through the cannulated rod; and
  - a rotational feature coupled to the rod proximal end and configured to be rotated by an operator to rotate the cannulated rod to threadedly engage the cannulated rod with the posterior SI joint implant.

2. The insertion system of claim 1, wherein the insertion instrument further comprises:
- an outer shaft that receives the cannulated rod, the outer shaft comprising:
  - a shaft distal end comprising at least one coupling member for coupling to the posterior SI joint implant; and
  - a shaft proximal end.

3. The insertion system of claim 2,
- wherein the shaft proximal end comprises internal threads, and
- wherein the rod proximal end comprises a second set of external threads configured to threadedly engage with the internal threads to couple the cannulated rod to the outer shaft.

4. The insertion system of claim 1, further comprising:
- a joint sleeve configured to be inserted into an SI joint and to receive the insertion instrument therein, the joint sleeve comprising:
  - a first shoulder configured to engage with an ilium; and
  - a second shoulder configured to engage with a sacrum.

5. The insertion system of claim 4, wherein the first shoulder has a first height distinct from a second height of the second shoulder.

6. The insertion system of claim 1, wherein the rotational feature is a knob having an opening therethrough to provide access to the female luer lock.

7. An insertion system for inserting an implant, comprising:
- a guidewire;
- an insertion instrument, comprising:
  - a cannulated rod configured to be inserted over the guidewire and to be coupled to the implant, comprising:
    - a rod distal end for coupling to the implant; and
    - a rod proximal end having a syringe connector,
    - wherein the syringe connector is configured to couple to a syringe, thereby fluidly coupling the syringe, the insertion instrument, and the implant such that bone graft is deployable into the implant by the syringe and through the cannulated rod when the cannulated rod and the implant are coupled.

8. The insertion system of claim 7, wherein the rod distal end comprises at least one first coupling feature for coupling the cannulated rod to the implant.

9. The insertion system of claim 8, further comprising:
- a shaft that receives the cannulated rod, the shaft comprising:
  - a shaft distal end comprising at least one second coupling feature for coupling the shaft to the implant.

10. The insertion system of claim 9,
- wherein the at least one first coupling feature comprises threads, and
- wherein the at least one second coupling feature comprises at least one prong.

11. The insertion system of claim 9, wherein the rod proximal end comprises external threads that mate with internal threads on a shaft proximal end of the shaft.

12. The insertion system of claim 7, wherein the implant is a posterior sacroiliac (SI) joint implant and further comprising:
- a joint sleeve configured to be inserted into an SI joint space and to receive the cannulated rod during insertion of the posterior SI joint implant, the joint sleeve comprising:
  - a first shoulder configured to abut against an ilium;
  - and a second shoulder opposite the first shoulder and that is configured to abut against a sacrum.

13. The insertion system of claim 12, wherein the first shoulder comprises a first height distinct from a second height of the second shoulder.

14. The insertion system of claim 7, wherein the guidewire comprises nitinol.

15. A method for posterior sacroiliac (SI) joint fusion, comprising:
- providing an insertion instrument comprising:
  - a cannulated rod having a rod distal end and a rod proximal end comprising a luer lock;
- creating a minimally invasive incision on a patient to provide posterior access to an SI joint of the patient;
- inserting a guidewire through the minimally invasive incision and into the SI joint of the patient;
- coupling the insertion instrument to a posterior SI joint implant;
- inserting, using the insertion instrument and through the minimally invasive incision, the posterior SI joint implant into the SI joint;

coupling a syringe to the rod proximal end via the luer lock such that the syringe is fluidly connected to the insertion instrument and the posterior SI joint implant; and filling, using the syringe and through the insertion instrument, the posterior SI joint implant with bone graft.

16. The method of claim 15, further comprising:

prior to inserting the posterior SI joint implant into the SI joint, inserting a joint sleeve through the minimally invasive incision, over the guidewire, and into the SI joint.

17. The method of claim 16, wherein the joint sleeve comprises a first shoulder configured to engage with an ilium and a second shoulder configured to engage with a sacrum.

18. The method of claim 15, wherein coupling the insertion instrument to the posterior SI joint implant comprises threadedly engaging a distal end of the cannulated rod with a proximal end of the posterior SI joint implant.

19. The method of claim 15, wherein the insertion instrument and the posterior SI joint implant are inserted over the guidewire.

20. The method of claim 15, further comprising:

pre-filling the posterior SI joint implant with the bone graft before inserting the posterior SI joint implant into the SI joint.

* * * * *